United States Patent
Kaplan et al.

(10) Patent No.: US 10,213,593 B2
(45) Date of Patent: *Feb. 26, 2019

(54) METHOD AND APPARATUS FOR NONINVASIVE INHIBITION OF DEEP VEIN THROMBOSIS

(71) Applicant: StimMed LLC, Buffalo, NY (US)

(72) Inventors: Robert E. Kaplan, Buffalo, NY (US); James J. Czyrny, Amherst, NY (US); Scott E. Friedman, Amherst, NY (US)

(73) Assignee: StimMed LLC, Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/287,531

(22) Filed: Oct. 6, 2016

(65) Prior Publication Data

US 2017/0021157 A1 Jan. 26, 2017

Related U.S. Application Data

(63) Continuation-in-part of application No. 15/204,625, filed on Jul. 7, 2016, which is a continuation of
(Continued)

(51) Int. Cl.
  *A61N 1/04* (2006.01)
  *A61N 1/36* (2006.01)
(52) U.S. Cl.
  CPC ......... *A61N 1/0456* (2013.01); *A61N 1/0452* (2013.01); *A61N 1/36003* (2013.01); *A61N 1/36021* (2013.01)
(58) Field of Classification Search
  CPC ................ A61N 1/0456; A61N 1/0452; A61N 1/36003; A61N 1/36021
(Continued)

(56) References Cited

U.S. PATENT DOCUMENTS 2,003,392 A 6/1935 Rucker
3,204,637 A 9/1965 Frank et al.
(Continued)

FOREIGN PATENT DOCUMENTS

CN 101102810 A 1/2008
CN 201001437 1/2008
(Continued)

OTHER PUBLICATIONS

Lindstrom et al. Electrically induced short-lasting tetanus of the calf muscles for prevention of deep vein thrombosis. Br J Surg. Apr. 1982;69(4):203-6.
(Continued)

*Primary Examiner* — Catherine Voorhees
*Assistant Examiner* — Roland Dinga
(74) *Attorney, Agent, or Firm* — Knobbe Martens Olson & Bear LLP

(57) ABSTRACT

System, device and method for providing neuromuscular electrical stimulation (NMES) to muscles of foot. The device includes an electrical signal generator for producing a wave pattern of variable frequency, duration, intensity, ramp time and on-off cycle. The device further includes surface electrodes for being positioned over the foot muscles or around ankles and attached to the signal generator. The device includes a wearable device for positioning a first electrode adjacent a heel of the wearer's foot and a second electrode adjacent an arch of the foot. The signal generator is programmed to stimulate the foot muscles and nerves. Location of the electrodes and the programming are adjusted to reduce pooling of the blood in the soleal veins of the calf and enhance venous blood flow to prevent deep vein thrombosis (DVT); to enhance venous blood flow for the post-thrombotic syndrome patient; to expedite wound healing; to reduce neuropathic pain of the foot and ankle, chronic
(Continued)

musculoskeletal pain of the ankle and foot, and acute post-operative foot and ankle pain; and to prevent muscular atrophy of the foot muscles.

19 Claims, 26 Drawing Sheets

Related U.S. Application Data application No. 12/687,935, filed on Jan. 15, 2010, now abandoned.

(58) Field of Classification Search
USPC .......................................................... 607/144
See application file for complete search history.

(56) References Cited

U.S. PATENT DOCUMENTS

| | | | |
|---|---|---|---|
| 3,344,792 A | 10/1967 | Offner et al. | |
| 3,472,233 A | 10/1969 | Sarbacher | |
| 4,509,521 A | 4/1985 | Barry | |
| 4,558,704 A | 12/1985 | Petrofsky | |
| 4,580,569 A | 4/1986 | Petrofsky | |
| 4,622,973 A | 11/1986 | Agarwala | |
| RE32,940 E * | 6/1989 | Gardner | A61H 9/0078 128/DIG. 20 |
| 5,097,833 A | 3/1992 | Campos | |
| 5,342,410 A | 8/1994 | Braverman | |
| 5,358,513 A | 10/1994 | Powell, III et al. | |
| 5,407,418 A | 4/1995 | Szpur | |
| 5,556,422 A | 9/1996 | Powell, III | |
| 5,643,331 A | 7/1997 | Katz | |
| 5,674,261 A | 10/1997 | Smith | |
| 5,674,262 A | 10/1997 | Tumey | |
| 5,782,893 A | 7/1998 | Dennis, III | |
| 5,814,093 A | 9/1998 | Stein | |
| 5,891,065 A | 4/1999 | Caripa | |
| 6,002,965 A | 12/1999 | Katz et al. | |
| 6,132,387 A | 10/2000 | Gozani et al. | |
| 6,615,080 B1 * | 9/2003 | Unsworth | A61N 1/0452 607/2 |
| 2002/0095098 A1 | 7/2002 | Marinello | |
| 2004/0267153 A1 | 12/2004 | Bergethon | |
| 2005/0119713 A1 | 6/2005 | Whitehurst et al. | |
| 2005/0187601 A1 | 8/2005 | Wang | |
| 2006/0085047 A1 | 4/2006 | Unsworth et al. | |
| 2007/0142891 A1 | 6/2007 | Stanley | |
| 2011/0178572 A1 | 7/2011 | Czyrny et al. | |
| 2013/0006322 A1 | 1/2013 | Tai | |

FOREIGN PATENT DOCUMENTS

| | | |
|---|---|---|
| DE | 3916994 | 11/1990 |
| JP | H11 235373 | 8/1999 |
| WO | WO 2011/118918 | 9/2011 |

OTHER PUBLICATIONS

Roenberg et al. Prophylaxis of postoperative leg vine thrombosis by low dose subcutaneous heparin or peroperative calf muscle stimulation: a controlled clinical trial. Br Med J. Mar. 22, 1975; 1 (5959): 649-651.

European Search Report for Application No. EP 17 19 0046 dated Jun. 20, 2018.

* cited by examiner

METHOD AND APPARATUS FOR NONINVASIVE INHIBITION OF DEEP VEIN THROMBOSIS

INCORPORATION BY REFERENCE TO ANY PRIORITY APPLICATIONS

This application is a continuation-in-part application of U.S. patent application Ser. No. 15/204,625, filed on Jul. 7, 2016 which is a continuation of U.S. patent application Ser. No. 12/687,935, filed on Jan. 15, 2010, all of which are hereby incorporated by reference in their entirety.

BACKGROUND OF THE INVENTION

Field of the Invention

The present invention pertains generally to the field of the electrical stimulation of muscles for prevention of thrombosis and for pain management and, more particularly, to electrical stimulation of muscles of the foot.

Description of the Related Art

Electrical stimulation of muscles and nerves by applying electrodes over the skin is currently used for enhancing blood circulation and reducing blood clots and for scrambling the pain signal that reach the brain in order to manage pain.

Patients undergoing surgery, anesthesia and extended periods of bed rest or other inactivity are often susceptible to a condition known as deep vein thrombosis, or DVT. DVT is a clotting of venous blood in the lower extremities or pelvis. This clotting occurs due to the absence of muscular activity required to pump the venous blood in the lower extremities, local vascular injury, or a hypercoagulable state. The condition can be life-threatening if a blood clot migrates to the lung, resulting in pulmonary embolism (PE), or otherwise interferes with cardiovascular circulation. More generally, venous thromboembolic disease (VTED) is a cause of significant morbidity and mortality for individuals immobilized after orthopedic surgery, due to neurologic disorders, even during prolonged travel, and a variety of other conditions.

Since 1954, it has been known that prolonged dependency stasis, a state imposed by airplane flights, automobiles trips and even attendance at the theater may bring on thrombosis. In 1977, it was shown that trips as short as three to four hours could induce DVT and PE.

DVT and related conditions may be controlled or alleviated by assisting blood circulation (venous return) in the muscles.

Current approaches to prophylaxis include mechanical compression using pneumatic compression devices, anticoagulation therapy and electrical stimulation of the muscles. Pneumatic compression equipment is often too cumbersome for mobile patients, or during prolonged travel. Anticoagulation therapy carries the risk of bleeding complications and must be started several days in advance to be effective. Electric stimulation has advantages over the other two methods in that it can be started at the time prophylaxis is needed and can be portable using DC current sources.

A number of U.S. patents teach various methods of applying electrical stimulation to the calf muscle for the prevention of DVT. These include Powell, III, U.S. Pat. No. 5,358,513; Turney, U.S. Pat. No. 5,674,262; Dennis, III, U.S. Pat. No. 5,782,893; Katz, U.S. Pat. No. 5,643,331; and Katz, U.S. Pat. No. 6,002,965.

U.S. Pat. No. 6,615,080 to Unsworth et al. provides a method for preventing DVT, PE, ankle edema and venostasis and a device that includes a single channel sequential neuromuscular electrical stimulation (NMES) unit. The NMES unit is battery powered and can be programmed to deliver a particular stimulus profile. In order to simplify the patient's ability to properly apply the NMES device, the stimulator generates biphasic symmetrical square wave pulses with stimulus parameters demonstrated to result in optimum venous blood flow. The stimulus profile included a stimulus frequency fixed at 50 pulses per second, a stimulus duration of 300 microseconds, a ramp up time of 2 seconds, a ramp down time of 2 seconds, and a stimulus cycle set at 12 seconds on and 48 seconds off. Once set in advance by the doctor, manufacturer or user, the patient adjusts the intensity, using a stimulus intensity dial, to the point needed to produce a minimally visible or palpable muscle contraction. The output leads of the stimulator are attached through a conductor to electrodes of various types including, self-adherent surface electrodes. These electrodes are of opposite polarity and create an electrical potential difference between themselves and the tissue that separates them. The frequency and electrical characteristics of electrical impulses applied to the patient is referred to as the electrical stimulation routine.

In published but abandoned U.S. Patent Application Publication No. 2006/0085047 A, a variation of Unsworth et al. provided a method of automatically controlling the delivery of single channel NMES of the plantar muscle, in response to the sensing of motion of the foot or leg. In the published application, the stimulation is turned off during walking or running to prevent slips or falls and to reduce power consumption of the unit that provides the stimulation.

FIG. 1A, FIG. 1B, FIG. 1C, FIG. 1D, and FIG. 1E show muscles of the sole of a foot.

There are four layers of muscles in the sole of the foot. After the skin of the plantar region and the fatty tissue have been removed, an expansion of fibrous tissue known as the plantar fascia is visible. If this is also taken away, the first layer of muscles is exposed, consisting of abductor pollicis (14), flexor brevis digitorum (18), and the abductor minimi digiti (16) (FIG. 1A). The second layer, situated under the first, consists of the tendons of the flexors longus digitorum (11), proprius, and pollicis (12). On the outer side of the foot, the tendon of the peroneus longus (5) passes beneath the flexor accessories (20). To complete the layer, the muscles flexor accessorius (20) and the lumbricales (19) must be named (FIG. 1B). The third plantar layer consists of the tendon of tibialis posticus (10), the flexor brevis pollicis (15), the adductor pollicis (21), the flexor brevis minimi digiti (17), and, running across the foot, the transversus pedis (22). The sheath of the peroneus longus (5), and the plantar ligament, are also found in this layer (FIG. 1C). The fourth layer (FIG. 1F) consists of three interossei (23), one on the inner side of the second toe, and the others each on the inner side of the third and fourth toes.

They draw to the central line XY, called the "central muscular action line," or the "line of muscular action." The first layer (FIG. 1E) on the dorsal surface consists of the tendons of the tibialis anticus (1), extensor proprius pollicis (2), extensor longus digitorum (3), and the tertius peroneus (4). The muscles of the extensor brevis digitorum (13), after passing under the extensor longus digitorum (3), divide into four tendons, and aid in the extension of the toes. The second layer (FIG. 1D) consists of four interossei (23a), fixed on the outer side of the second, third, and fourth toes and drawing from the "central muscular action line" XY, and one on the inner side of the second toe drawing to line XY.

Muscles of the foot are also divided into a plantar group (internal, external, and central), which pertains to the sole of the foot, and a dorsal group, which indicates the back muscles behind the plantar muscles.

The dorsal group includes:
13. Extensor brevis digitorum. First layer.
23a. Interossei dorsal (4). Second layer.

The plantar group includes:
14. Abductor pollicis. Internal first layer.
15. Flexor brevis pollicis. Internal third layer.
16. Abductor minimi digiti. External first layer.
17. Flexor brevis minimi digiti. External third layer.
18. Flexor brevis digitorum. Central first layer.
19. Lumbricales. Central second layer.
20. Flexor accessorius. Central second layer.
21. Adductor pollicis. Central third layer.
22. Transversus pedis. Central third layer.
23. Interossei plantar (3). Fourth layer.

The location and function of each muscle is further described below.

13. The extensor brevis digitorum arises in the upper outer side of the heel-bone, and, broadening out, it passes under the extensor longus digitorum, when it divides into four tendons that go forward and are inserted in the bases of the first phalanges. Its action is to aid the extension of the toes and to counteract the tendency of obliquity of the extensor longus digitorum.

14. The abductor pollicis arises on the inner posterior region of the os calcis, and is inserted in the first phalanx of the great toe. Its action is to abduct the big toe away from the central line of the foot to the imaginary line that forms the centre of the body. By this action, the great toes would be brought closer together.

15. The flexor brevis pollicis comes from the second row of the tarsus, and is inserted to the base of the first phalanx.

16. The abductor minimi digiti arises from the outside of the os calcis, and goes forwards to the external side of the first phalanx of the little toe. Its action is to draw the little toe away from the middle line of the foot.

17. The flexor brevis minimi digiti has origin in the sheath of the peroneus longus and the base of the fifth metatarsal bone, and is inserted in the first phalanx of the little toe. Its action is to flex the little toe.

18. The flexor brevis digitorum, from the heel-bone and the plantar fascia, draws down the toes, and is inserted in the second phalanges of the four toes.

19. The four lumbricales are affixed to the inner side of the four toes. Their action is to draw the toes into the inner side of the foot.

20. The flexor accessorius extends from the os calcis to the second, third, and fourth toes. In contraction, it counteracts the obliquity of the flexor longus digitorum, hence its name.

21. The adductor pollicis arises from the sheath of the peroneus longus and the third and fourth metatarsals, and is inserted in the first phalanx of the great toe on the outer side. Its action is to adduct, or draw, the great toe to the central line of the foot.

22. The transversus pedis goes across the foot, and is inserted in the phalanx of the great toe. Its office is to adduct, or draw, the big toe to the line of the foot termed the "line of muscular action."

23. The three plantar interossei are situated between the bones of the toes on the inner side, and draw to the central line the three outer toes.

23a. The four interossei, on the dorsal surface of the foot, are situated on the outer side of the bones of the toes, and draw the third and fourth toes away from the central line of muscular action. The two interossei on either side of the second toe draw away from the axis of the toe either to the outer or inner side of the foot, respectively.

The foot is provided with two kinds of nerves—those that supply the skin with sensory branches, and the other sort that give motor impressions to the muscles. The posterior tibial and the anterior tibial nerves come from the sciatic nerve, the former giving branches to the muscles in passing down to the inner side of the ankle. The posterior tibial then divides into external plantar nerves and internal plantar nerves, that supply the toes and sole of the foot. The anterior tibial nerves supply the dorsum of the foot as well as the outer side of the leg.

Under the skin are found pads of fat, at the heel and toes especially.

The muscles of the foot are further classified as either intrinsic or extrinsic. The intrinsic muscles are located within the foot and cause movement of the toes. These muscles are flexors (plantar flexors), extensors (dorsiflexors), abductors, and adductors of the toes. Several intrinsic muscles also help support the arches of the foot. The extrinsic muscles are located outside the foot, in the lower leg. The powerful calf muscle is among them. Most of these muscles have long tendons that cross the ankle, to attach on the bones of the foot and assist in movement.

FIG. 2 shows the flexor digitorum brevis muscle.

This muscle is responsible for flexing the four smaller toes. It lies in the middle of the sole of the foot, immediately above the central part of the plantar aponeurosis, with which it is firmly united. Its deep surface is separated from the lateral plantar vessels and nerves by a thin layer of fascia. It arises by a narrow tendon, from the medial process of the tuberosity of the calcaneus, from the central part of the plantar aponeurosis, and from the intermuscular septa between it and the adjacent muscles. It passes forward, and divides into four tendons, one for each of the four lesser toes.

Of the other muscle of the first layer, the abductor digiti minimi (abductor minimi digiti, abductor digiti quinti) is a muscle which lies along the lateral border of the foot, and is in relation by its medial margin with the lateral plantar vessels and nerves. Its function is to flex and abduct the fifth (little) toe. The last muscle of the first layer, abductor pollicis is like the abductor digiti minimi except that it lies along the lateral inside border of the foot and connects to the big toe.

FIG. 3A and FIG. 3B show placement of electrodes as disclosed by Unsworth et al., U.S. Pat. No. 6,615,080.

FIG. 3A illustrates a sole of a foot 31. Toes 32, ball 33, arch 34, and heel 35 are shown in the drawing. Electrodes 36a, 36b are located in an area over intrinsic muscles on the plantar surface of the foot, or proximal to them, for example on or around the ball of the foot 33, and over or proximal to the heel 35. In FIG. 3A, electrodes 36a and 36b are placed that deliver the electrical impulses generated by the NMES device 30. FIG. 3B shows an alternate area 36a' at which an electrical impulse can be delivered. In some embodiments of the Unsworth invention, the electrode 36a occupies only the area of the ball of the foot, while other embodiments include elliptical electrodes having their major axis normal to the longitudinal axis of the foot 31.

As shown in FIG. 3A and FIG. 3B, the Unsworth issued patent applies one electrode over or proximal to the heel and the other over the intrinsic muscles on the plantar surface of the foot, for example, on or around the ball of the foot. In Unsworth, the intensity of the electrical stimulation required is only that necessary to create a slight visible muscle twitch of the foot muscles, or a minimally visible or palpable muscle contraction. By stimulating in this manner, blood pooling in the calf veins was prevented.

Electrical stimulation is also utilized for pain management. The most common form of electrical stimulation used for pain management is transcutaneous electrical nerve stimulation (TENS) therapy, which provides short-term pain relief. Electrical nerve stimulation and electrothermal therapy are used to relieve pain associated with various conditions, including back pain. For example, intradiscal electrothermal therapy (IDET) is a treatment option for people with low back pain resulting from intervertebral disc problems. In TENS therapy for pain management, a small, battery-operated device delivers low-voltage electrical current through the skin via electrodes placed near the source of pain. The electricity from the electrodes stimulates nerves in the affected area and sends signals to the brain that "scramble" normal pain perception. TENS is not painful and has proven to be an effective therapy to mask pain.

SUMMARY OF THE INVENTION

Aspects of the present invention provide systems, devices, and methods for providing neuromuscular electrical stimulation (NMES) to muscles of the foot. One aspect provides a single channel stimulator device that includes an electrical signal generator for producing a wave pattern of variable frequency, duration, intensity, ramp time, and on-off cycle. The stimulator device further includes surface electrodes for being positioned over the foot muscles and attached to the signal generator. The signal generator is programmed to stimulate the foot muscles. The programming is adjusted to reduce pooling of the blood in the soleal veins of the calf and enhance venous blood flow to prevent DVT, to enhance venous blood flow for the post-thrombotic syndrome patient, to expedite wound healing, to reduce neuropathic pain of the foot and ankle, chronic musculoskeletal pain of the ankle and foot, and acute post-operative foot and ankle pain, and to prevent muscular atrophy of the foot muscles.

In some aspects of the present invention, the electrodes are arranged on the heel and the mid-section or arch of the foot. This arrangement is appropriate for systems, devices, and methods of the present invention that contribute to (1) enhanced venous blood flow to prevent DVT, (2) enhanced venous blood flow for the post-thrombotic syndrome patient, and (3) prevention of muscular atrophy of the foot muscles.

As FIG. 3A and FIG. 3B of the drawings show, in Unsworth, one electrode is located on the heel while the second electrode targets the ball of the foot.

Aspects of the present invention place the second electrode in the arch of the foot. This location targets the flexor digitorum brevis muscle. This muscle is the largest muscle; it is close to the skin and is separated from the lateral plantar vessels and nerves by a thin layer of fascia, and it is responsible for flexing the four smaller toes. Because it is a larger muscle, it generates more circulation when it is stimulated, and because it is closer to the skin, it is more accessible by the electrode. Moreover, one end of this muscle is located at the heel, and the electrical pulse may be conducted through the length of the muscle and the nerves that control it.

The ball of the foot and its vicinity are separated from the skin with a thicker layer of fat, and the skin is generally more calloused in that area. The arch of a normal foot is seldom calloused and has a relatively thin skin. Moreover, the lumbricals, which are located under the ball, lie in the second layer of foot muscles, which is located deeper and further from the skin. Lumbricals are much smaller than the flexor digitorum brevis and control the same 4 small toes. Except, the motion generated by the lumbricals is an adduction motion, which is not as extensive as a flexing motion, and generally would not generate as much circulation.

The electrodes are located on the heel and the bottom of the mid-foot region or the arch. The active electrode is located at the mid-foot region, and the ground electrode is located at the heel.

Aspects of the present invention further provide systems, devices, and methods that contribute to (1) enhanced wound healing, (2) reduction of the neuropathic pain of the foot and ankle, (3) reduction of the chronic musculoskeletal pain of the ankle and foot, and (4) reduction of the acute post-operative foot and ankle pain. These aspects of the present invention provide pain relief by generating a tapping feeling that results from intermittent electrical stimulation of the muscle. For reduction of neuropathic pain, chronic musculoskeletal pain, acute post-op pain, and wound healing, the electrodes are placed at the level of the main ankle bones called the medial malleolus and the lateral malleolus. For both electrodes, the connection site would be just below the malleolus. For other indications, the electrodes are located on the sole of the foot.

Aspects of the present invention provide a device for delivering electrical stimulation to muscles of a foot of a patient. The device includes one or more power sources, a signal generator for generating electrical current, and electrodes in communication with the signal generator for delivery of the electrical current to the foot. The electrical current is for causing the muscles to contract, and the electrodes are adapted to be located on a heel of the foot and on an arch of the foot.

Aspects of the present invention provide a device for delivering electrical stimulation to muscles of a foot of a patient. The device includes one or more power sources, a signal generator for generating electrical current, and electrodes in communication with the signal generator for delivery of the electrical current to the foot. The electrical current is for disturbing pain signals communicated by the muscles to brain, and the electrodes are connected anteriorly to ankle to stimulate peroneal nerve of the foot. The electrodes may be adapted to be located at two or more of medial ankle at location of posterior tibial nerve, lateral ankle at location of sural nerve, and anterior ankle at location of anterior tibial nerve.

Aspects of the present invention provide a method for enhancing venous blood flow to prevent deep vein thrombosis, enhancing venous blood flow for post-thrombotic syndrome patients, and preventing muscular atrophy of foot muscles. The method includes connecting electrodes to a foot of the patient, and applying electrical current of a programmable waveform, intensity, frequency, and duration to the foot muscles through the electrodes. A ground electrode is connected to a heel of the foot, and a positive electrode is connected to an arch of the foot.

Aspects of the present invention provide a method for enhancing wound healing, reducing neuropathic pain of the foot and ankle, reducing chronic musculoskeletal pain of the ankle and foot, and reducing acute post-operative foot and ankle pain. The method includes connecting electrodes to a foot of the patient, and applying electrical current of a programmable waveform, intensity, frequency, and duration to the foot muscles through the electrodes. The electrodes are connected anteriorly to the ankle to stimulate peroneal nerve of the foot. The electrodes may be connected at two or more of just below the medial malleolus at posterior tibial nerve, at lateral malleolus at sural nerve, and at anterior ankle at anterior tibial nerve.

Aspects of the present invention provide a wearable device for positioning a first electrode adjacent a heel of a wearer's foot and a second electrode adjacent an arch of the foot, comprising 1) a flexible support having a bottom portion configured to extend along a least a portion of the bottom of the foot, posteriorly from an arch, and around the heel; 2) an ankle portion of the support configured to extend upwardly along the back of the wearer's foot from the heel; 3) a foot strap carried by the support, configured to secure the bottom portion to the bottom of the foot; 4) an ankle strap carried by the support, configured to secure the ankle portion to the wearer's ankle; 5) a heel electrode carried by the bottom portion; and 6) an arch electrode carried by the bottom portion. In other aspects of the present invention, the wearable device may further comprise a control carried by the electrical connectors.

In some aspects of the present invention, the bottom portion may comprise a central longitudinal axis, and at least a portion of each of the heel electrode and the arch electrode may reside on both sides of the axis. Each of the heel electrode and the arch electrode may intersect the central longitudinal axis.

In some aspects of the present invention, each of the heel electrode and the arch electrode may have a geometric center that is within about 0.1, 0.2, 0.3, 0.4, 0.5, 0.6, 0.7, 0.8, 1.0, or 1.5 inches of the longitudinal axis. In one aspect of the present invention, the geometric centers of the heel electrode and the arch electrode may be within 0.5 inches of the longitudinal axis.

In some aspects of the present invention, the arch electrode may have a surface area of at least about 25%, 50%, 100%, 150%, 200%, 250%, 300%, 400%, 500%, or 600% of the surface area of the heel electrode. In one aspect of the present invention, the arch electrode may have a surface area of at least about 150% of the surface area of the heel electrode.

In other aspects of the present invention, each of the heel electrode and the arch electrode has a geometric center and the geometric centers are spaced apart along the longitudinal axis by a distance within the ranges of from about 3.5 inches to about 4.5 inch, or from about 3 inch to about 5 inches. In one aspect of the present invention, the spacing between the geometric centers of the heel electrode and the arch electrode is approximately 4 inches.

In other aspects of the present invention, each of the heel electrode and the arch electrode may further comprise a releasable electrically conductive pad positioned to contact the foot of the wearer.

In yet another aspect of the present invention, the support may comprise a first surface for contacting the patient and a second, opposing surface, and further comprising at least two electrical connectors on the second surface. The electrical connectors may comprise mechanical connectors for both mechanically and electrically connecting to a control. Further, the electrical connectors may be carried by the ankle portion of the support.

In some aspects of the present invention, each of the heel electrode and the arch electrode may have a transverse axis, extending at a normal angle to the longitudinal axis. The length of the arch transverse axis may be at least about 50%, 100%, 150%, 180%, 200%, 250%, 300%, 400%, or 500% of the length of the heel transverse axis. In one aspect of the present invention, the arch transverse axis is at least about 150% the length of the heel transverse axis. In another aspect of the present invention, the arch transverse axis may be at least about 180% the length of the heel transverse axis.

In some aspects of the present invention, the heel transverse axis is within the range of from about 1.5 inches to about 2.5 inch, from about 1.0 inch to about 3.0 inches, or from about 0.5 inches to about 3.5 inches. In one aspect of the present invention, the heel transverse axis is within the range of from about 1.5 inches to about 2.5 inches in length.

In other aspects of the present invention, the arch transverse axis is within the range of from about 3.5 inches to about 4.5 inch, from about 3 inch to about 5 inches, from about 2.5 inches to about 5.5 inches, from about 2 inches to about 6 inches. In one aspect of the present invention, the arch transverse axis is within the range of from about 3 inches to about 5 inches in length.

DETAILED DESCRIPTION OF THE PREFERRED EMBODIMENT

Aspects of the present invention provide an improved system, device, and method of administering electrical stimulation to the muscles of the foot.

Aspects of the present invention provide a programmable electrical pulse generator for delivering an electrical current of mild and tolerable intensity to the muscles of the foot, which results in a mild contraction of the muscles. In various aspects of the present invention, the contraction may be accomplished by placing surface electrodes on the soles of the feet or at the ankles. When placed on the soles, the active surface electrodes are placed over the larger muscles of the first layer that are closer to the surface of the skin and in an area where callousing of the skin and the fat layer is minimal such as the mid-foot and arch area. The ground electrodes may be placed over or proximal to the heel. By stimulating the foot muscles in this manner, blood pooling in the calf veins is prevented. When placed on the side or top of the ankles, the surface electrodes stimulate the posterior tibial, the anterior tibial, or the sural nerves. By stimulating the peripheral nerves with the arrangement of electrodes around the ankles, pain management and improved wound healing may be achieved.

Figure 1A:
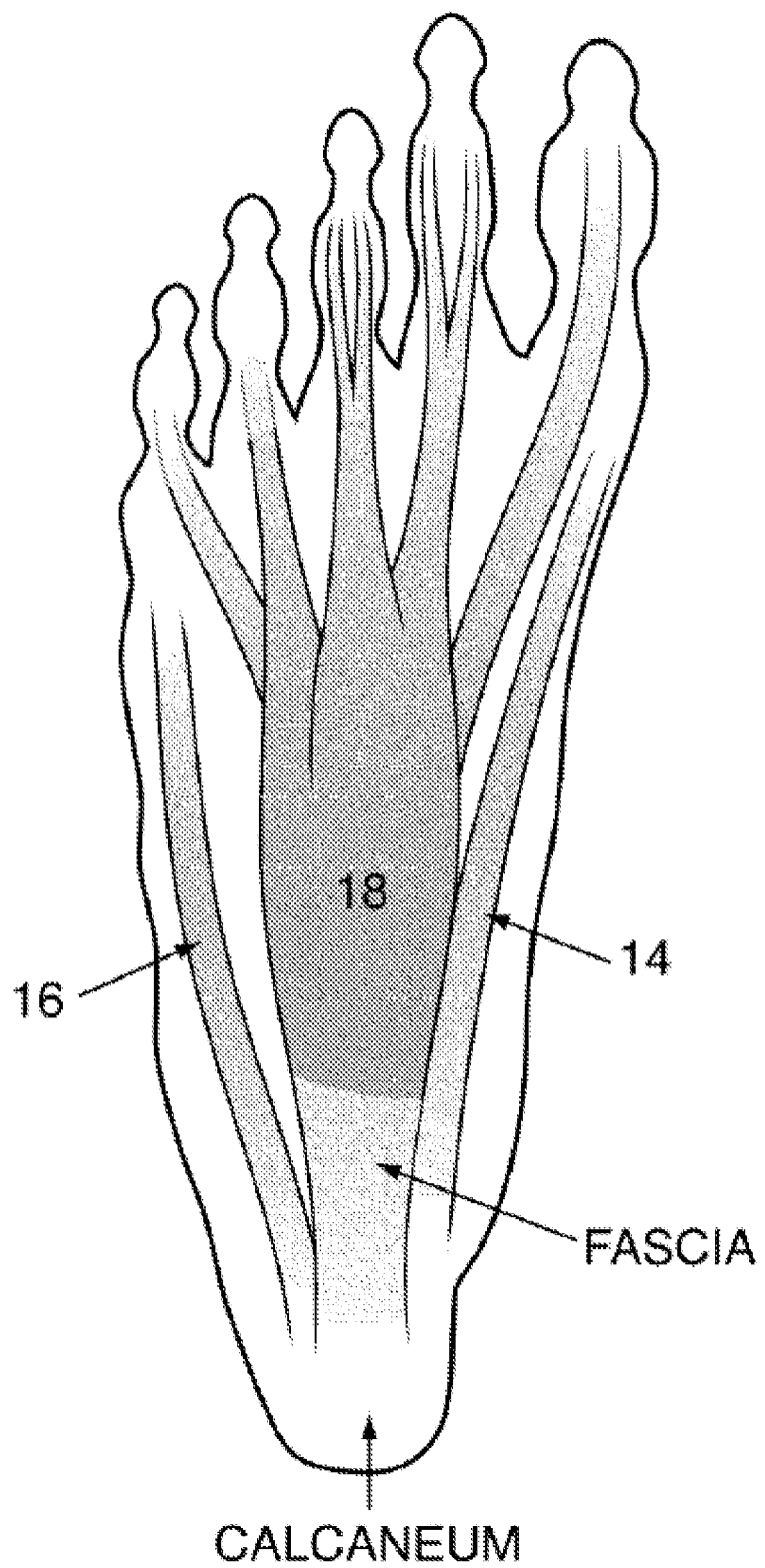
FIG. 1A, FIG. 1B, FIG. 1C, FIG. 1D, FIG. 1E and FIG. 1F show muscles of the sole of a foot.
Figure 1B:
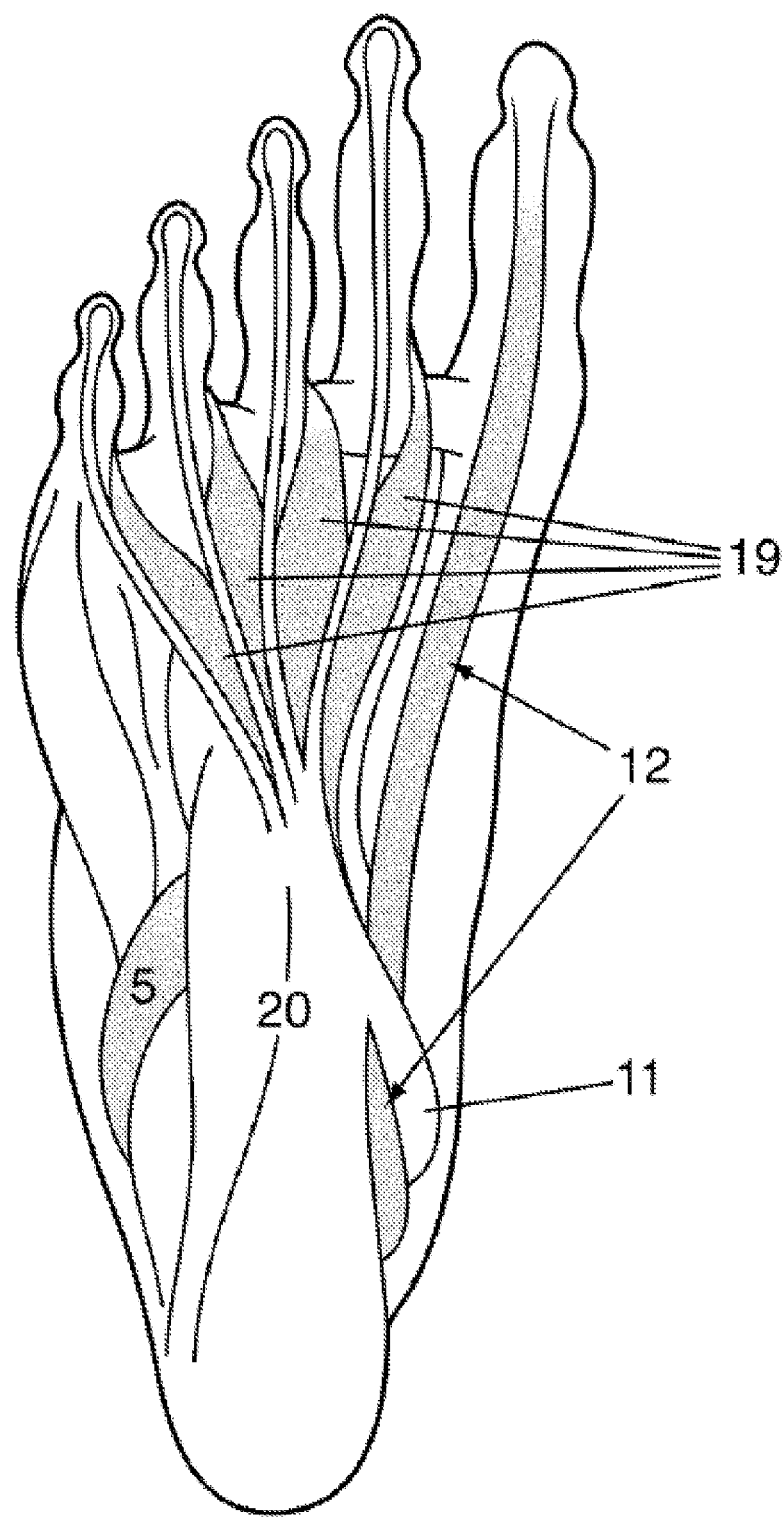
Figure 1C:
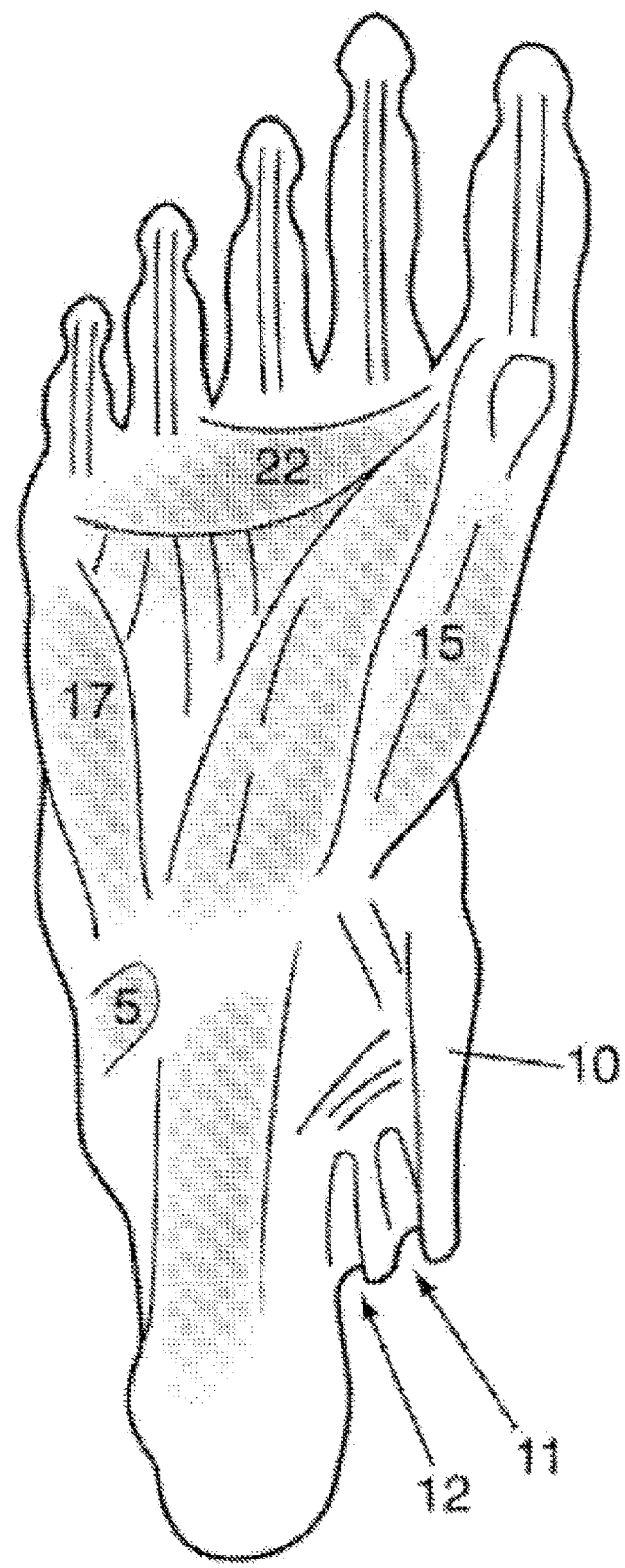
Figure 1D:
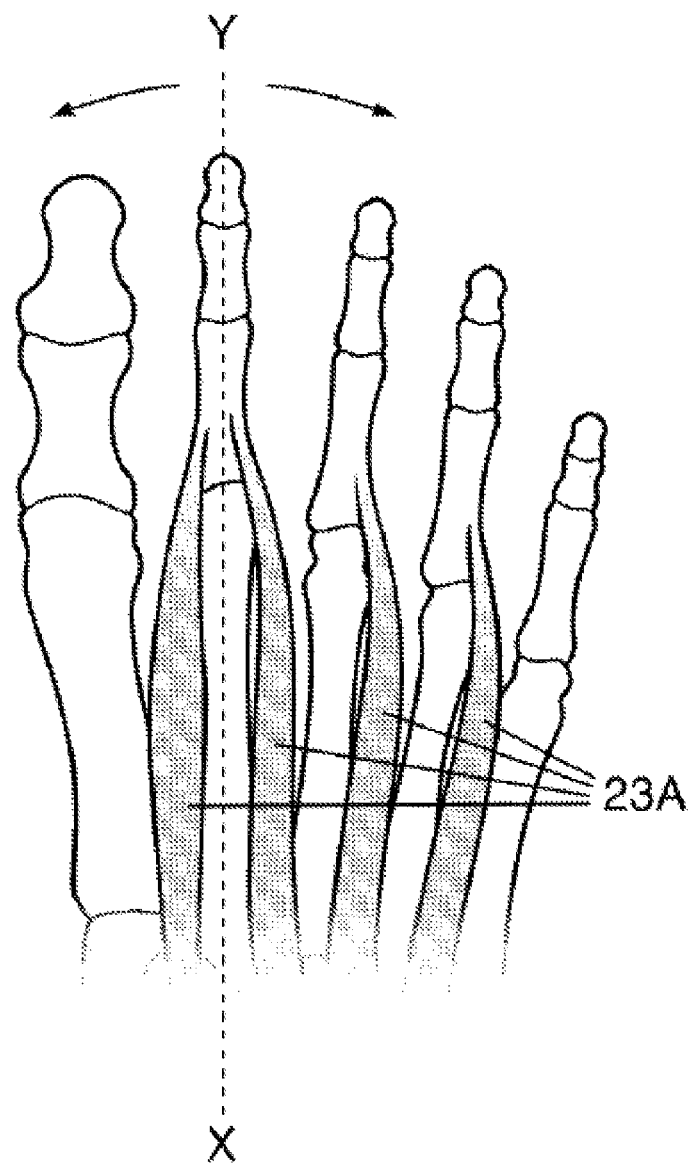
Figure 1E:
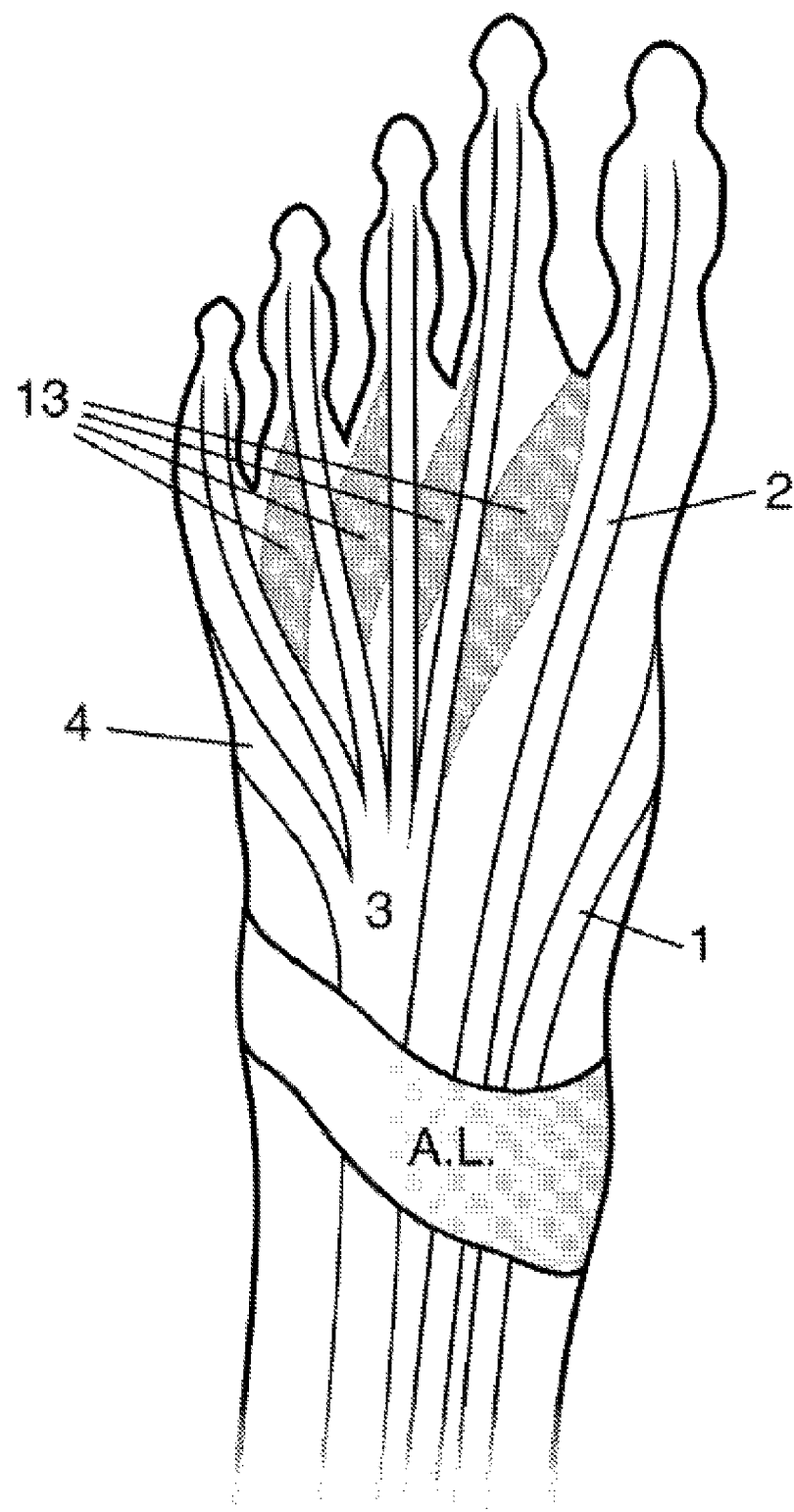
Figure 1F:
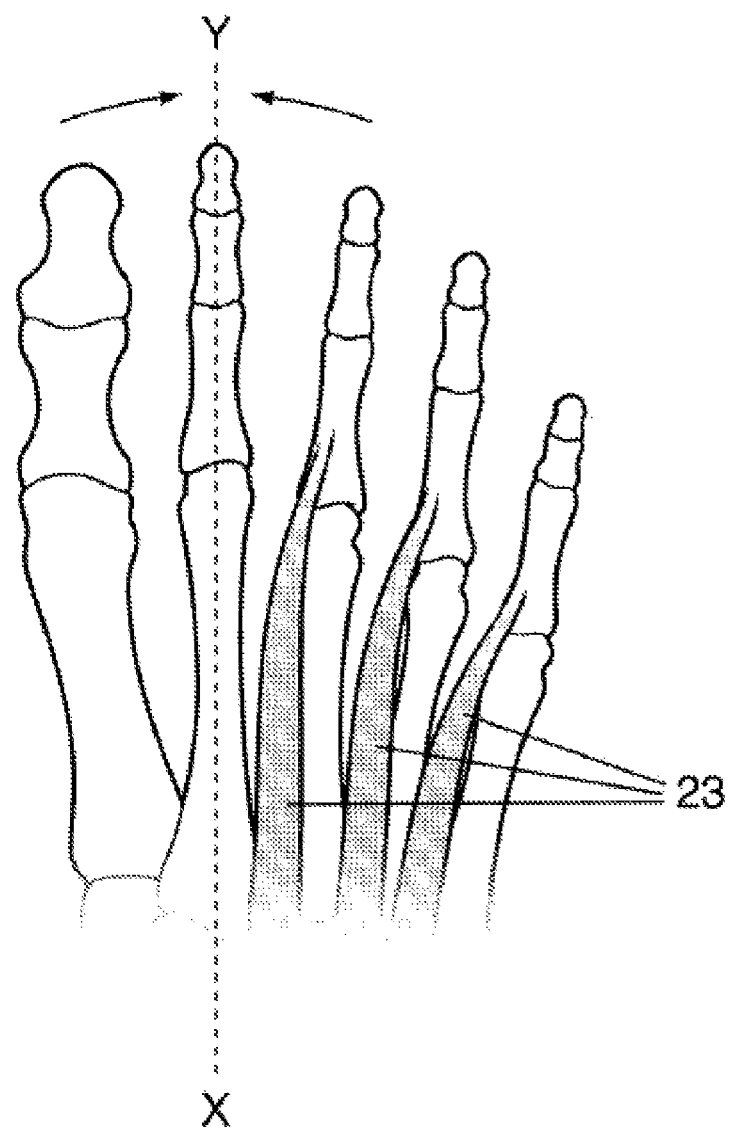
Figure 2:
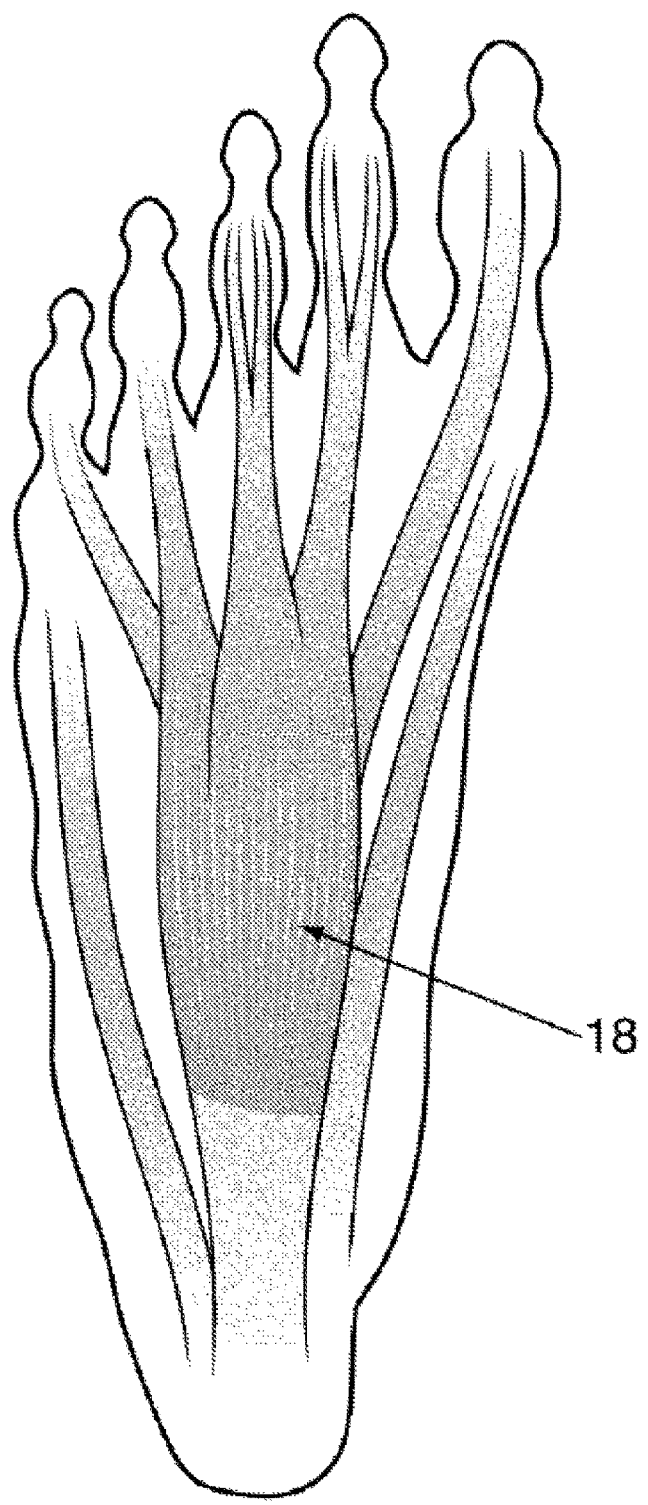
FIG. 2 shows the flexor digitorum brevis muscle.
Figure 3A:
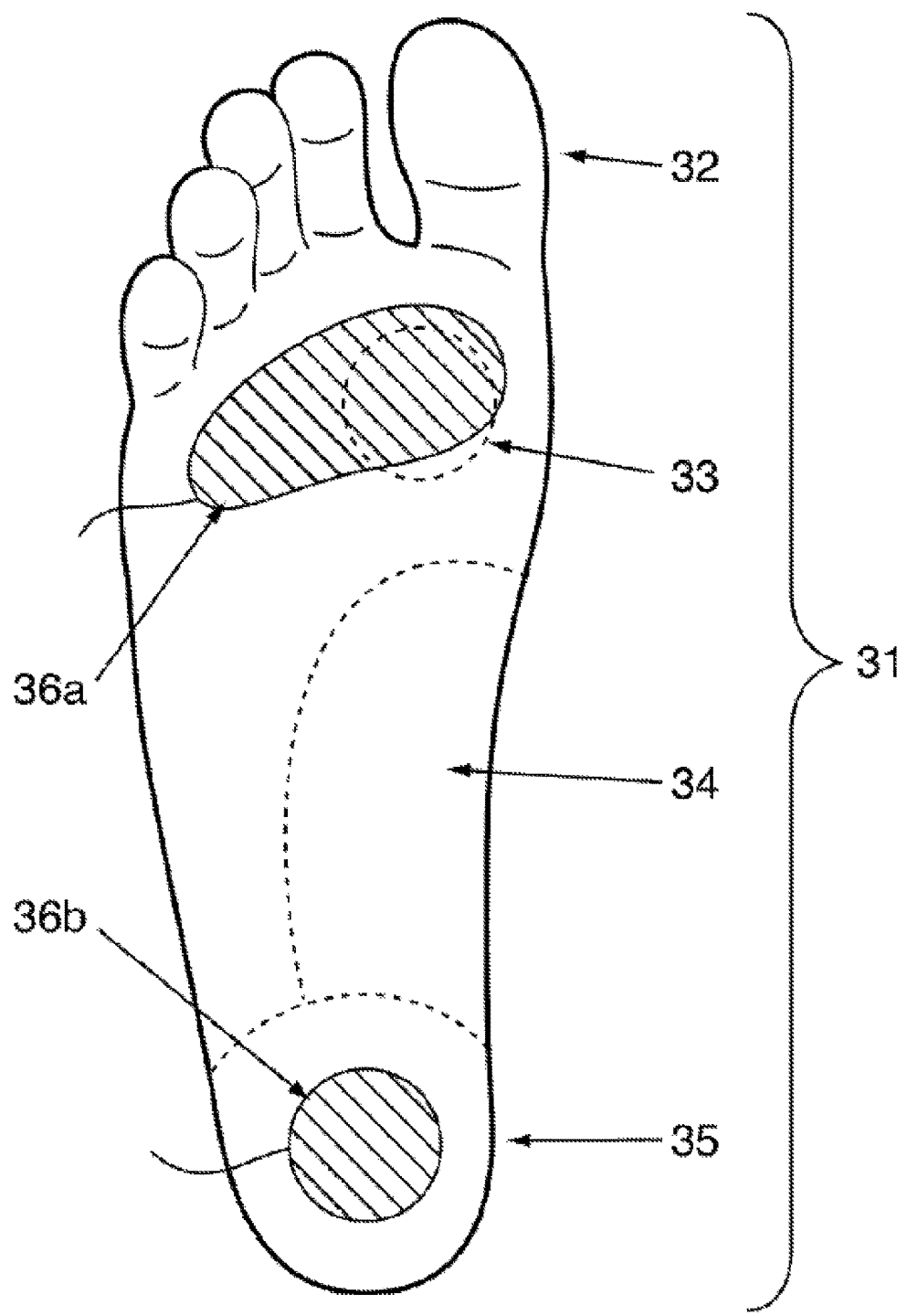
FIG. 3A and FIG. 3B show placement of electrodes as disclosed by Unsworth et al., U.S. Pat. No. 6,615,080.
Figure 3B:
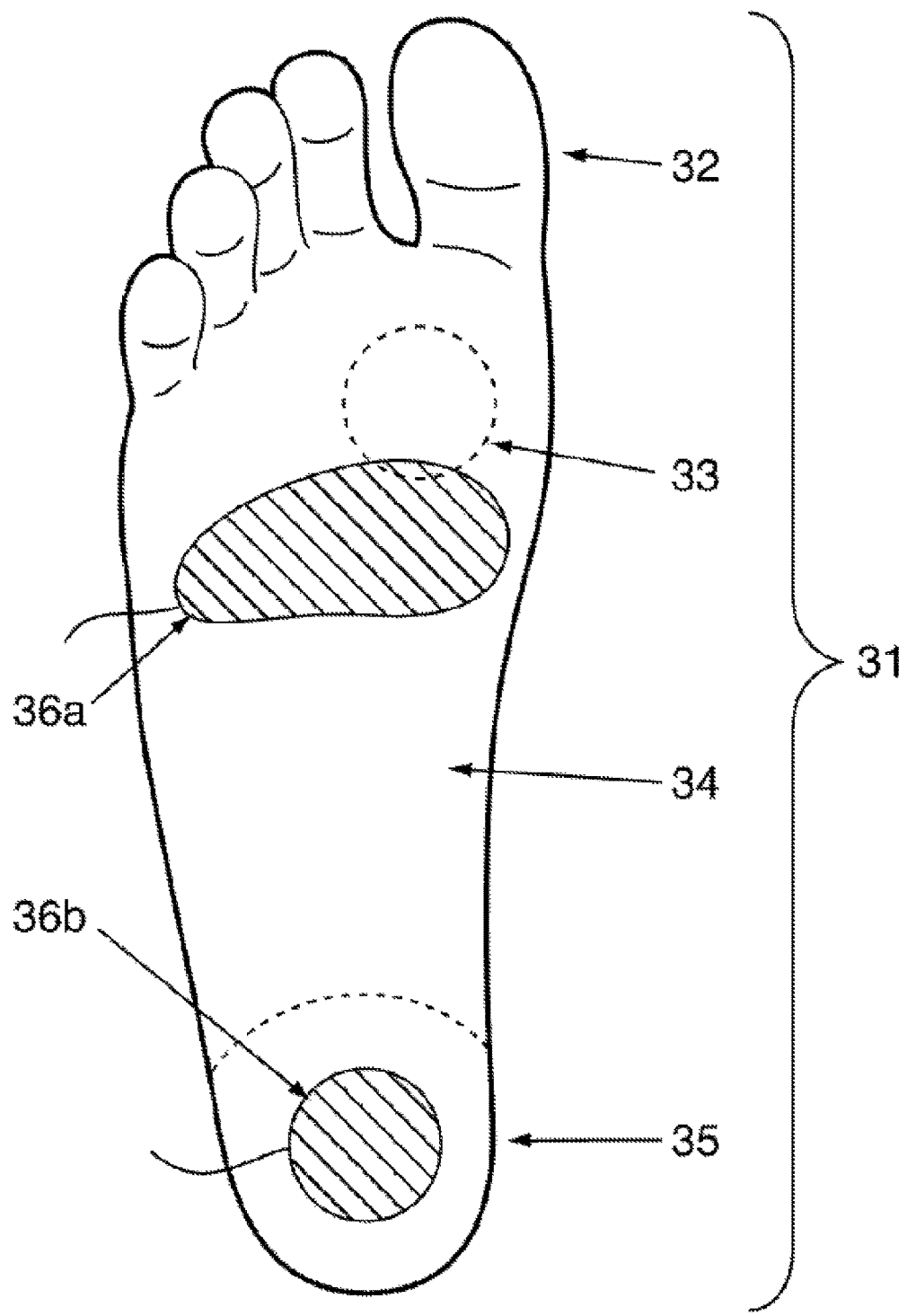
Figure 4:
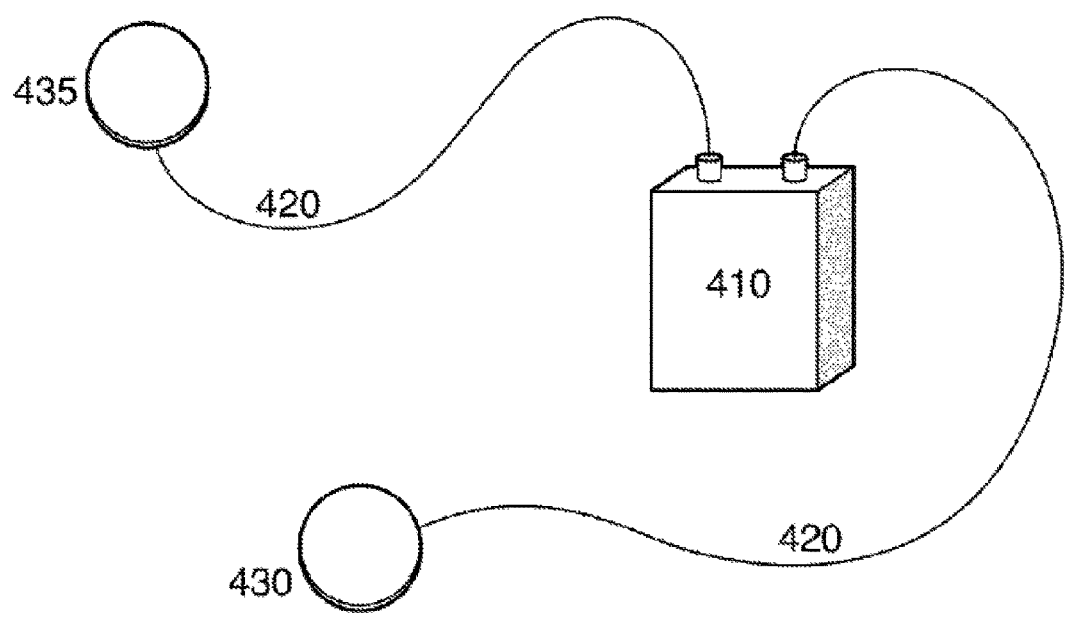
FIG. 4 shows a device for providing electrical stimulation to the foot, according to aspects of the present invention.
Figure 9:
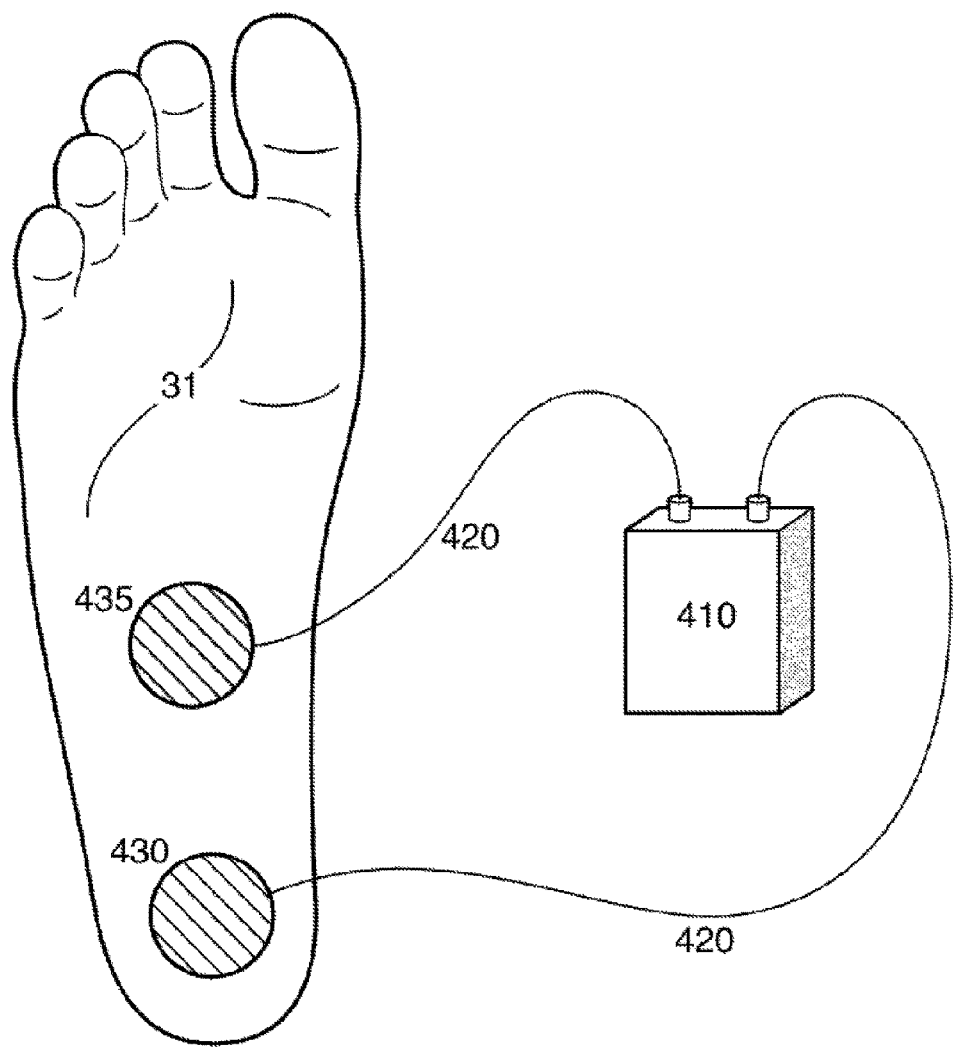
FIG. 9 shows a device for providing electrical stimulation to the foot, according to aspects of the present invention.

FIG. 4 and FIG. 9 show a device for providing electrical stimulation to the foot, according to aspects of the present invention.

The device 400 includes a generator 410, connecting wires 410, and electrodes 430 and 435. The electrodes are connected to the generator via the connecting wires. The generator 410 is a programmable electrical stimulation signal generation device. The electrodes 430 and 435 may be interchangeable and their polarity is determined according to their connection to the generator 410. The electrodes are self adhesive or otherwise attachable to skin.

Various aspects of the present invention may be implemented in footwear and accessories to footwear such as shoes, socks, and stockings. They may be carried in a pocket or pouch in an item of footwear, with conductors connecting the stimulus generating portion of the device to electrodes placed on the skin. The electrodes may vary in shape and size and may be self-adhering of the type utilized for TENS devices. Moreover, if at least one of the electrodes includes a power source, then the electrodes may be wirelessly in communication with the signal generator. In that situation, the signal generator may be located closer to the hands and head of the user, allowing him to more easily adjust the intensity and other parameters of the stimulation. In the case of wireless control, the electrodes must be connected together, outside the body, to create a closed circuit with the passage through the muscles. Further, the signal generator may be remotely programmable by a physician monitoring the patient.

Figure 5:
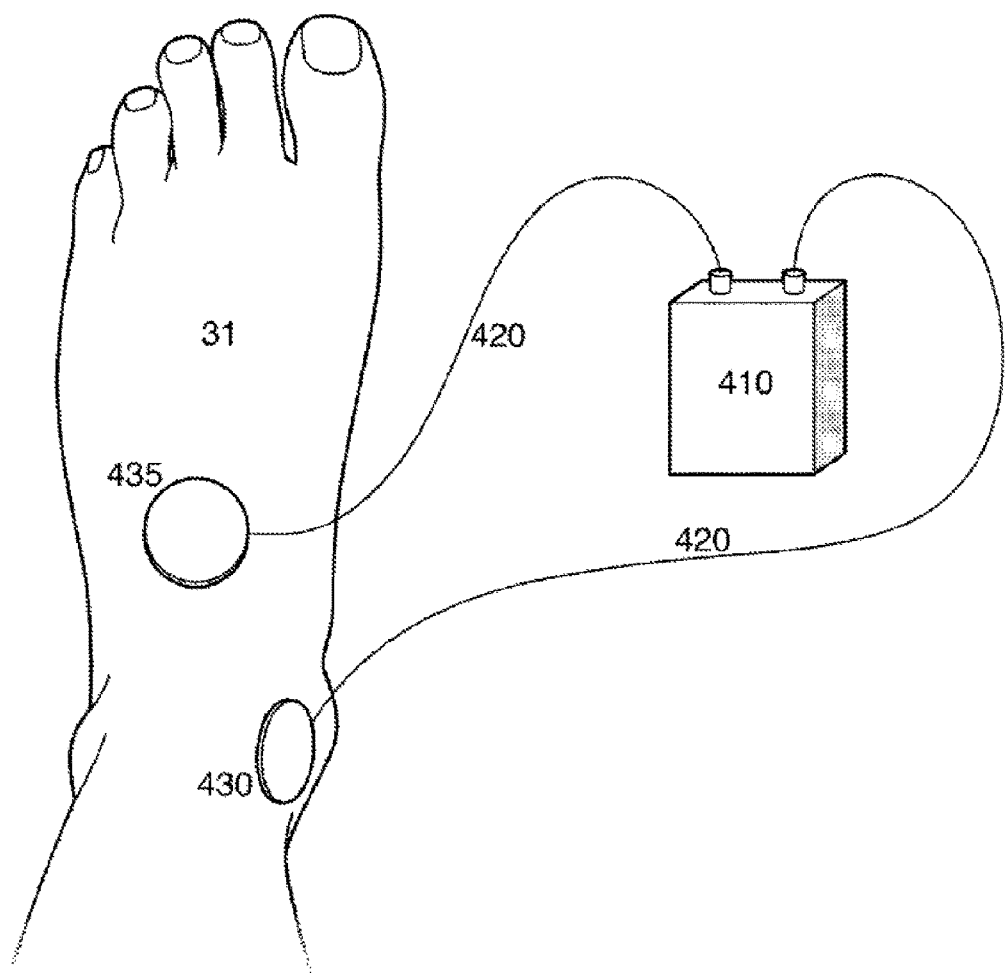
FIG. 5 shows placement of electrodes on the foot, according to aspects of the present invention.

FIG. 5 shows placement of electrodes on the foot, according to aspects of the present invention.

The electrodes 430 and 435 are located on the foot 31 such that one electrode attaches to the heel, and the other is attached to the mid-section or the big arch of the foot. In the arch area, the skin is not calloused, and the fat layer under the skin is minimal. In one aspect, the heel electrode 430 is the ground electrode, and the arch electrode is the active or positive electrode.

Figure 6A:
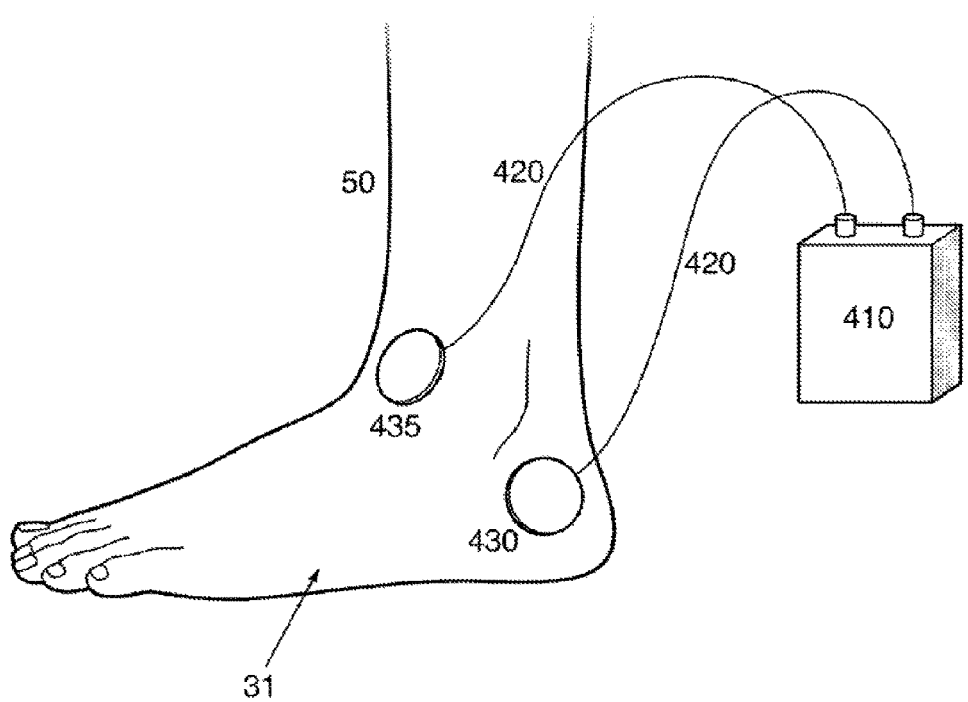
FIGS. 6A, 6B, and 6C show placement of electrodes on the foot for pain management, according to further aspects of the present invention.
Figure 6B:
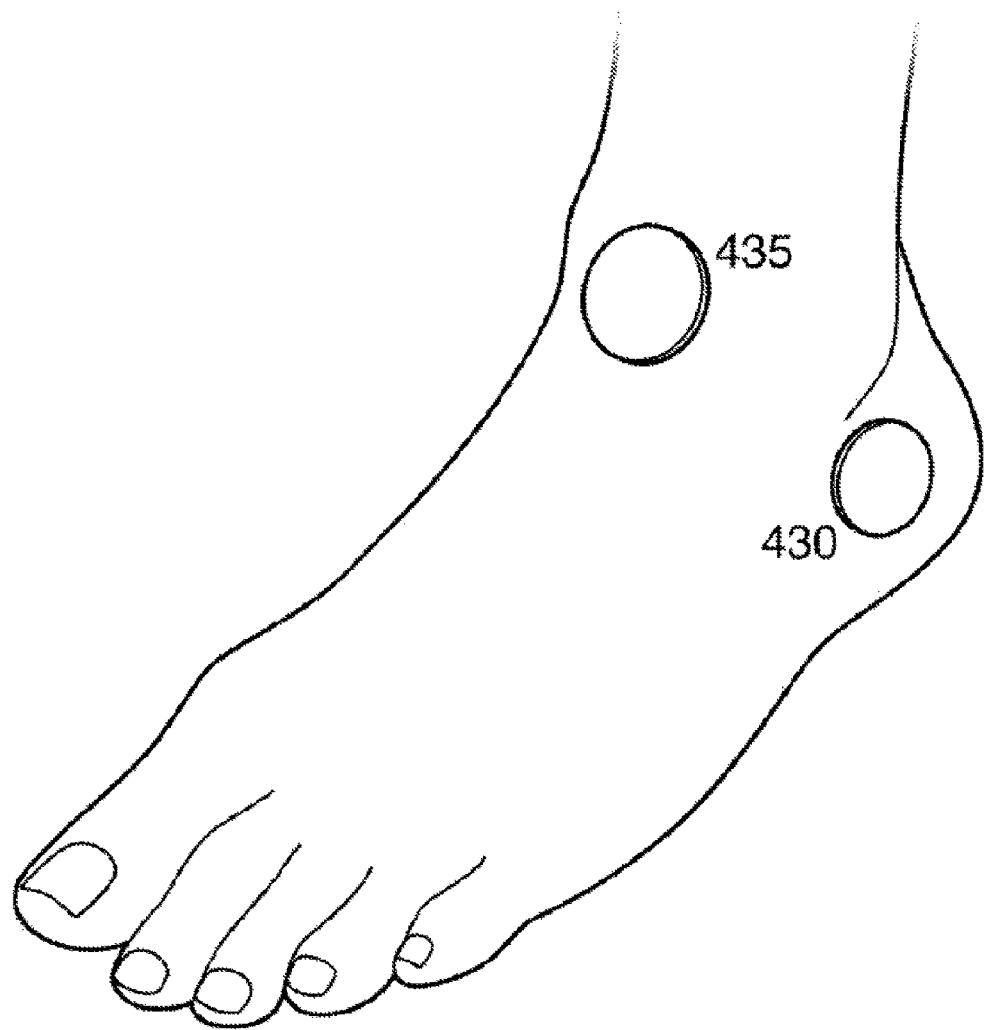
Figure 6C:
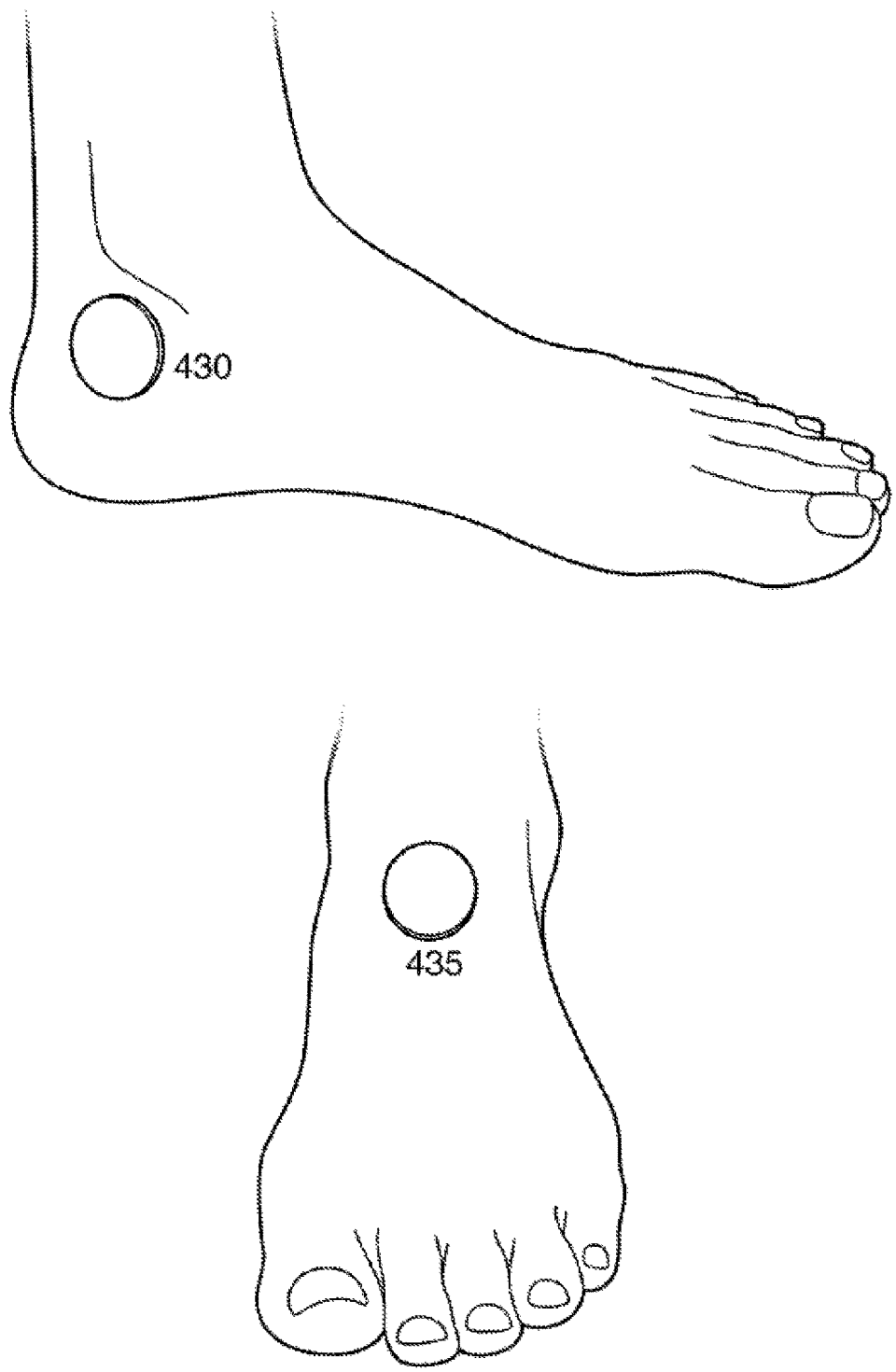

FIGS. 6A, 6B and 6C show placement of electrodes on the ankles, according to aspects of the present invention.

The placement of the ankle electrodes is chosen to optimally stimulate the posterior tibial, anterior tibial, and sural nerves of the leg 50. This in turn will provide the maximum therapeutic effect for pain management, enhancing wound healing, and preventing muscle atrophy. These electrodes may be located at the area of the peroneal motor nerve, which is also referred to as the anterior tibial nerve. In one aspect, the electrodes would be placed just lateral to the tendon of tibialis anterior and just proximal to the malleoli. FIG. 6B provides the ankle showing anterior electrode placement (435) and lateral electrode placement (430). FIG. 6C provides a line drawing of the ankle showing anterior electrode placement (435) and medial electrode placement (430).

Figure 7:
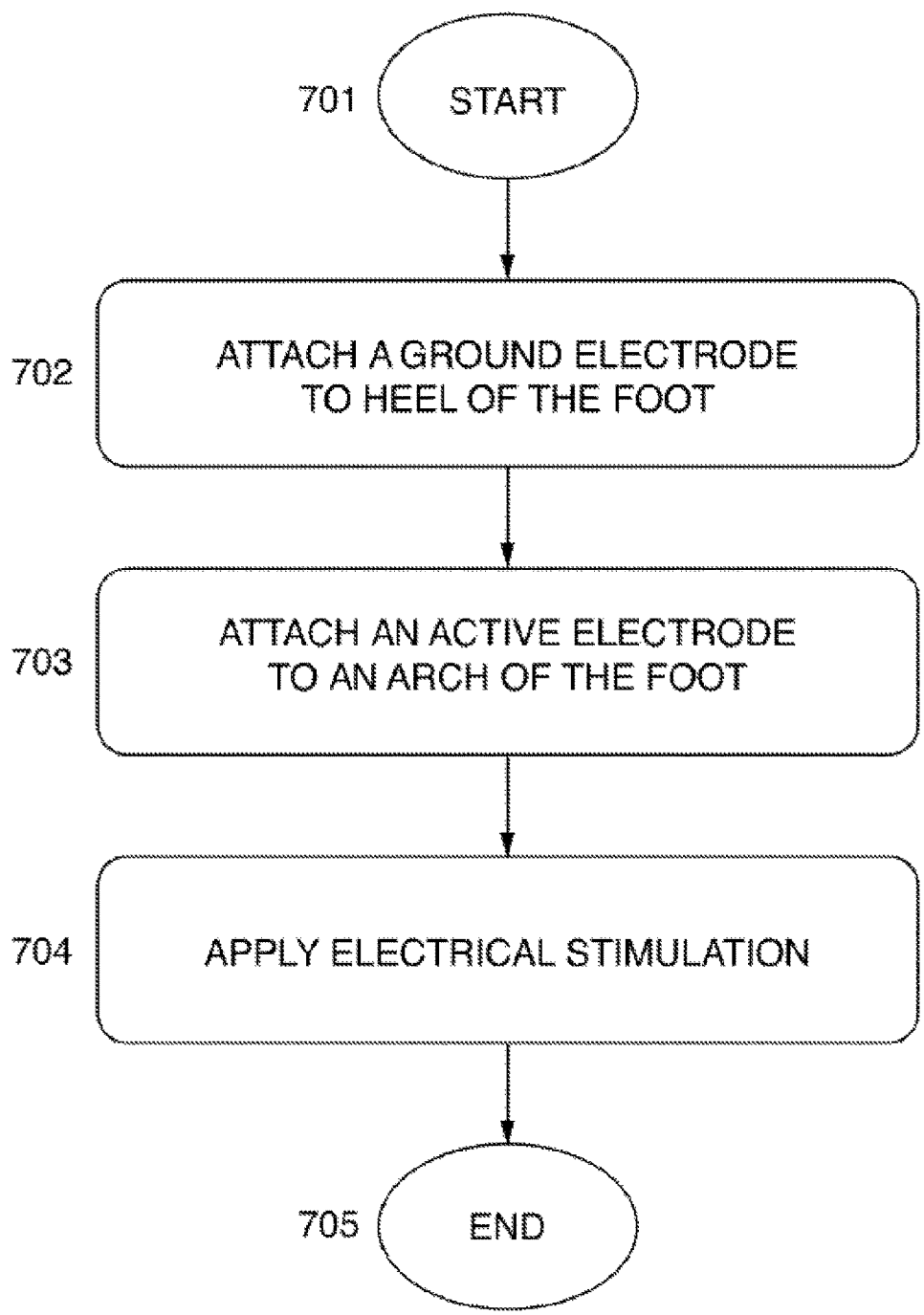
FIG. 7 shows a flowchart of a method of increasing circulation, according to aspects of the present invention.

FIG. 7 shows a flowchart of a method of increasing circulation, according to aspects of the present invention.

The method begins at 701. At 702, one electrode, for example the ground electrode, is connected to heel of a foot. At 703, the other electrode, for example the active electrode, is connected to a mid-section or arch of the foot. At 704, electrical stimulation is applied to the muscles of the foot through the attached electrodes. At 705, the method ends.

In variations of this method, the electrical stimulation may be periodically or continuously adjusted according to readout of parameters from the patient or according to decision of a physician or the patient himself.

Figure 8:
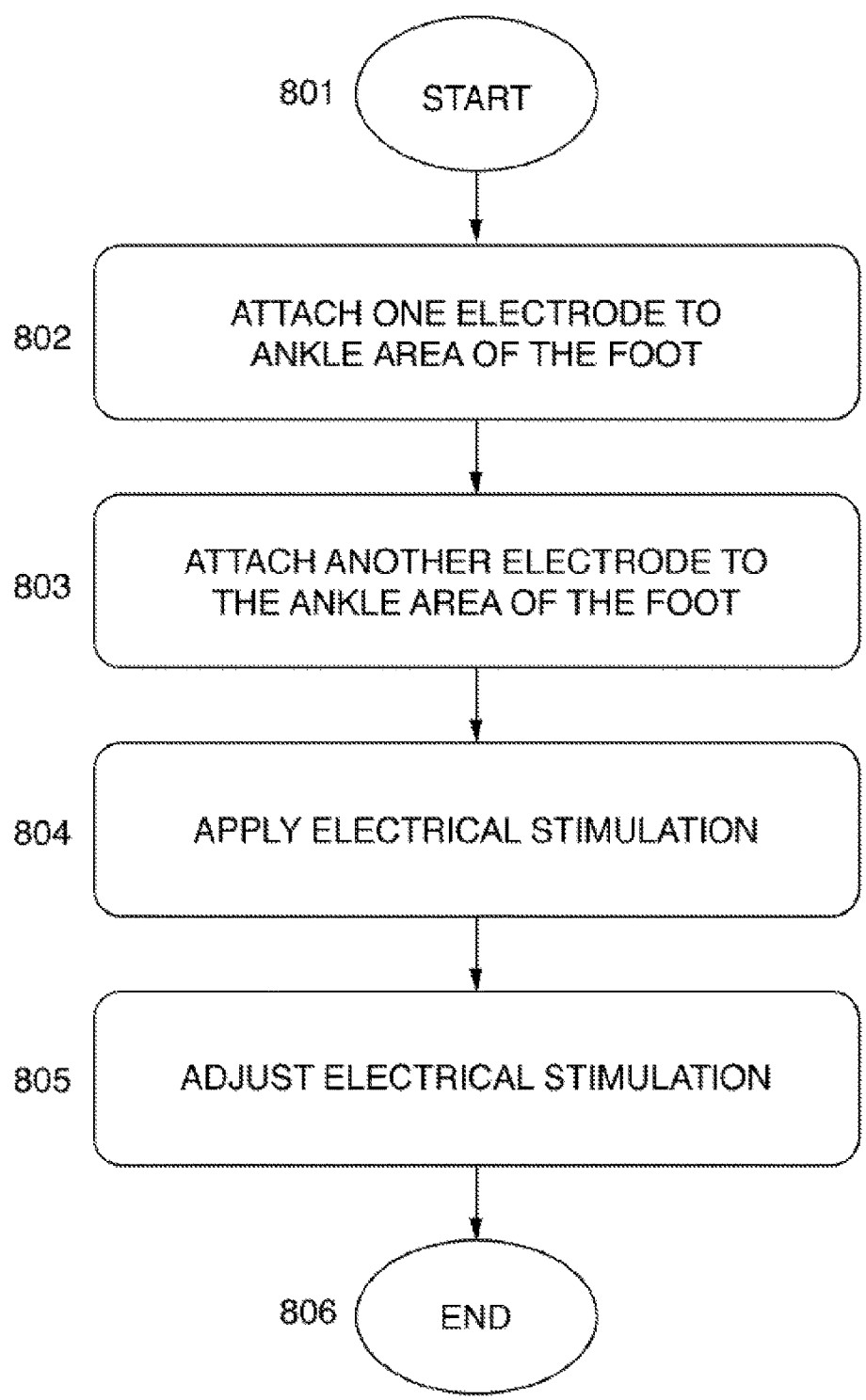
FIG. 8 shows a flowchart of a method of pain management, according to aspects of the present invention.

FIG. 8 shows a flowchart of a method of pain management, according to aspects of the present invention.

The method begins at 801. At 802, one electrode, for example the ground electrode, is connected above the ankle of a foot. At 803, the other electrode, for example the active electrode, is connected to below the ankle of the foot. At 804, electrical stimulation is applied to the muscles of the foot through the attached electrodes. At 805, the electrical stimulation is adjusted. At 806, the method ends.

Figure 10:
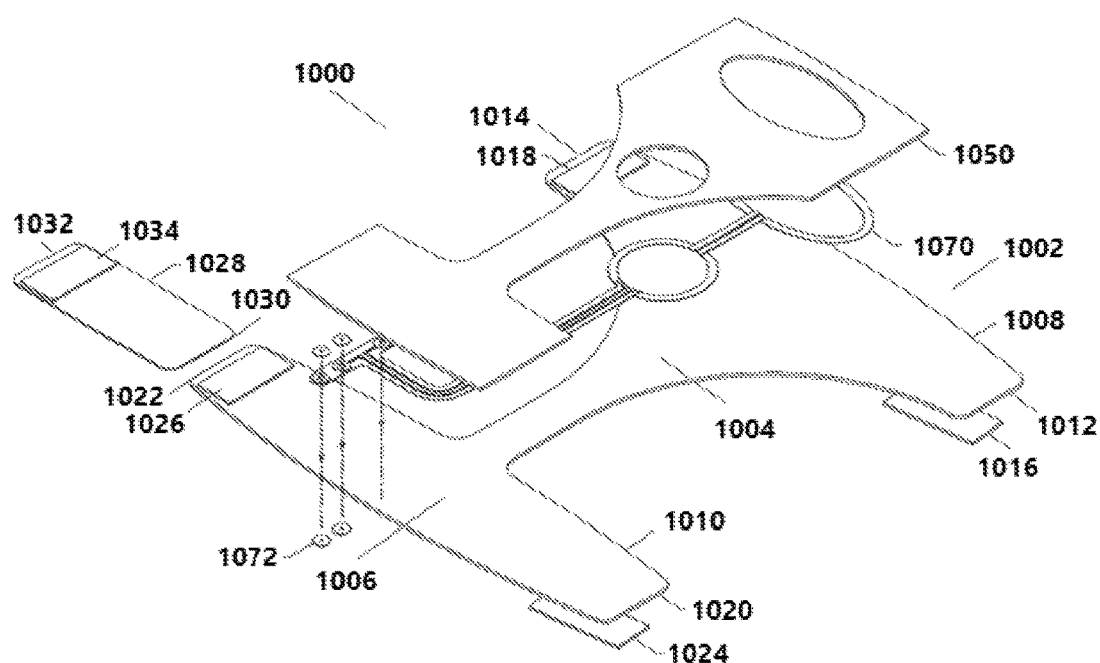
FIG. 10 shows an exploded perspective view of a wearable device for positioning a first electrode adjacent a heel of a patient's foot and a second electrode adjacent an arch of the foot, according to aspects of the present invention.

Aspects of the present invention provide a wearable device for positioning a first electrode adjacent a heel of the wearer's foot and a second electrode adjacent an arch of the foot. FIG. 10 shows an exploded perspective view of the wearable device 1000, according to aspects of the present invention.

Figure 11:
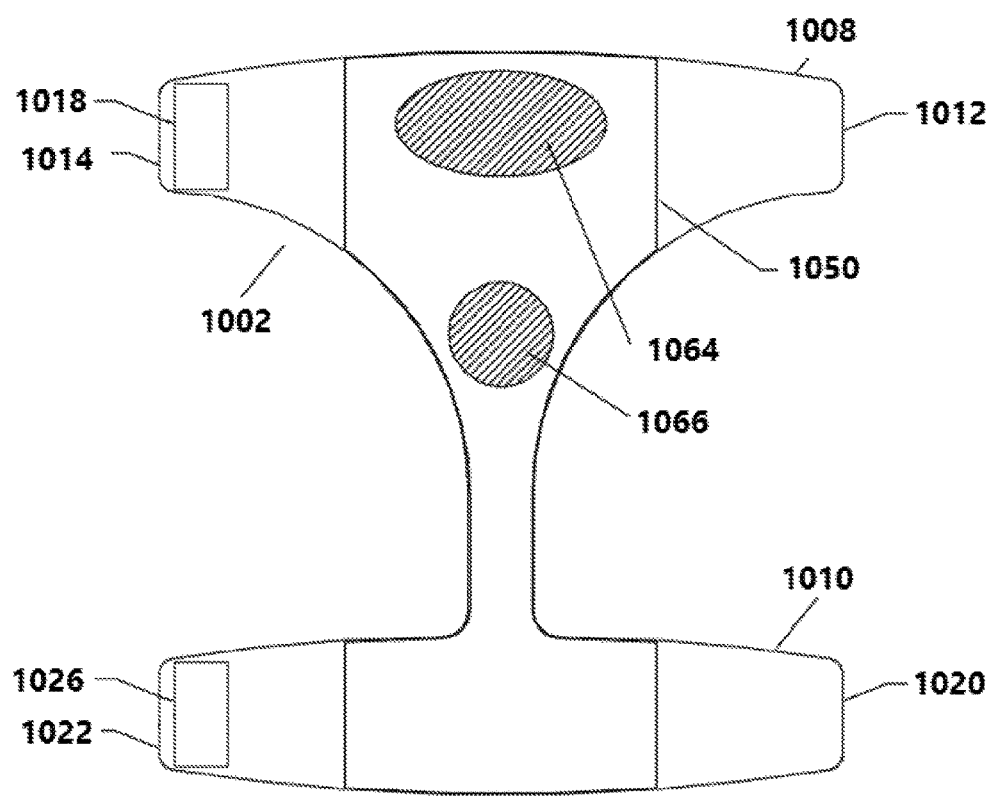
FIGS. 11 and 12 show inside and outside plan views, respectively, of a wearable device, according to aspects of the present invention.
Figure 12:
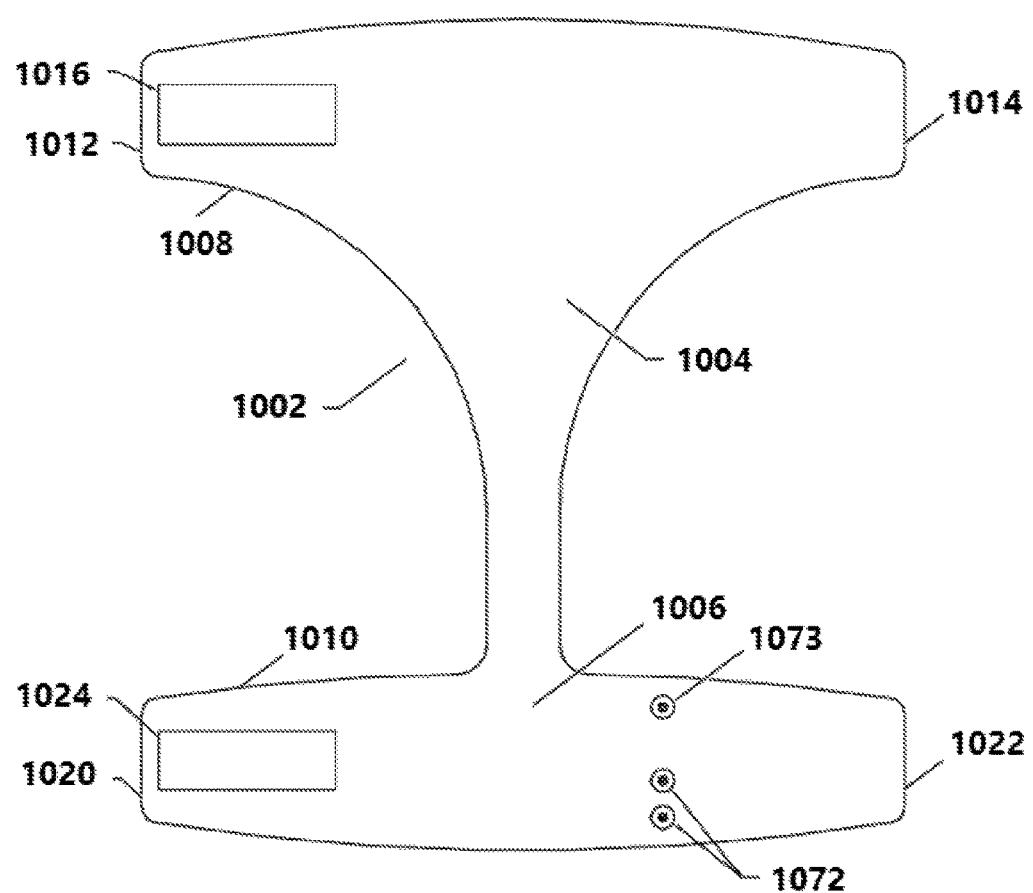
Figure 13:
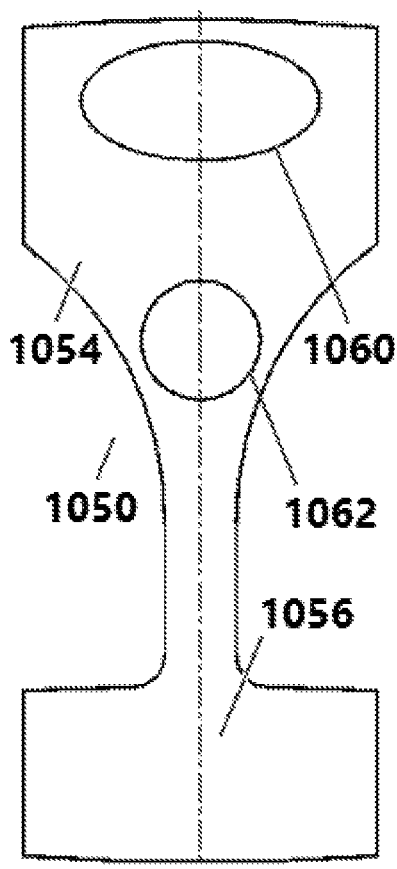
FIG. 13 shows an inside view of an inside cover of a wearable device, according to aspects of the present invention.
Figure 14:
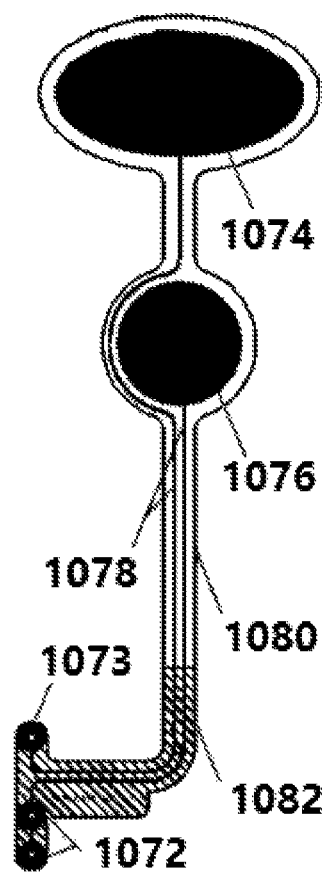
FIG. 14 shows an electrically conductive circuit image of a wearable device, according to aspects of the present invention.

The wearable device 1000 comprises an outside cover 1002, an inside cover 1050, and a circuit 1070. The inside cover 1050 is configured to contact the wearer's foot. FIGS. 11 and 12 show inside and outside views, respectively, of the wearable device 1000, according to aspects of the present invention. FIG. 13 shows an inside view of the inside cover 1050 of the wearable device 1000. FIG. 14 shows an image of the circuit 1070 of the wearable device 1000, according to aspects of the present invention.

Referring to FIGS. 10 and 12, the outside cover 1002 comprises a bottom portion 1004 and an ankle portion 1006. The bottom portion 1004 may be configured to extend along a least a portion of the bottom of the foot, posteriorly from an arch, and around the heel. The ankle portion 1006 may extend upwardly along the back of the wearer's foot from the heel. At least a portion of the outside cover 1002 is flexible such that it can extend along a least a portion of the bottom of the foot, posteriorly from an arch, around the heel, and/or upwardly along the back of the foot from the heel.

The outside cover 1002 may further comprise a foot strap 1008 and an ankle strap 1010. The foot strap 1008 secures the bottom portion 1004 to the bottom of the wearer's foot. The foot strap 1008 may extend around the middle of the foot to secure the bottom portion 1004 of the outside cover 1002 to the bottom of the foot. The ankle strap 1010 secures the ankle portion 1006 to the wearer's ankle. The ankle strap 1010 may extend in one or both directions to surround the ankle to secure the ankle portion 1006 of the outside cover 1002 to the ankle.

In the illustrated embodiment, the foot strap 1008 comprises a first wing 1012 and an opposing second wing 1014 for extending around the wearer's foot. Each end of the foot strap wings 1012, 1014 may have foot strap fasteners 1016, 1618 to hold the two ends of the foot strap 1008 together.

After the wearer places the foot strap 1008 around the middle of the foot, the wearer can use fasteners 1016, 1618 to hold the two ends of the strap together and keep the foot strap 1008 around the middle of the foot. The fasteners 1016, 1618 may be complementary structures such as interlocking loop and hook, snaps, buttons, adhesive, buckles, tri-glides, locks, rings, hooks or, sliders. For a foot strap 1008 without fasteners 1016, 1018, the wearer may tie a knot with the two ends of the foot strap 1008, or the foot strap 1008 may be a continuous strap optionally comprising an elastic material.

Similarly, two opposing wings 1020, 1022 of the ankle strap 1010 may each have complementary ankle strap fasteners 1024, 1026 to hold the ends of the ankle strap wings 1020, 1022 together. After the wearer places the ankle strap 1010 around the ankle, the wearer can use fasteners 1024, 1026 to hold the two ends of the strap together and keep the ankle strap 1010 around the ankle. The fasteners 1024, 1026 may be complementary structures such as interlocking loop and hook, snaps, buttons, adhesive, buckles, tri-glides, locks, rings, hooks or, sliders. For an ankle strap 1010 without fasteners 1024, 1026, the wearer may tie a knot with the two ends of the ankle strap 1010, or the ankle strap 1010 may be a continuous strap optionally comprising an elastic material.

The outside cover 1002 may further comprise an extender strap 1028. The extender strap 1028 may be attached to the foot strap 1008 or the ankle strap 1010 of the outside cover 1002. The extender strap 1028 extends the length of the foot strap 1008 or the ankle strap 1010 such that the foot strap 1008 or the ankle strap 1010 extends around the full circumference of the middle of the foot or the ankle, respectively. The extender strap 1028 may comprise a fastener 1034 configured such that its first end 1030 is fastened to a first end of the wings 1012, 1014 of the foot strap 1008 or the wings 1020, 1022 of the ankle strap 1010. The fastener 1034 may be configured to hold together its second, opposing end 1032 and the second, opposing end of the wings 1012, 1014 of the foot strap 1008 or the wings 1020, 1022 of the ankle strap 1010.

The inside cover 1050 is attached to the inside of the outside cover 1002. The outside surface of the inside cover 1050 is configured to abut the inside surface of the outside cover 1002 and may be secured by stitching, adhesives, heat bonding or other techniques. The inside surface of the inside cover 1050 is configured to touch the skin of the wearer's foot.

Referring to FIG. 13, the inside cover 1050 comprises a bottom portion 1054 and an optional ankle portion 1056. The bottom portion 1054 of the inside cover 1050 is attached to the bottom portion 1004 of the outside cover 1002. The bottom portion 1054 of the inside cover 1050 has two apertures 1060, 1062 on or near the central longitudinal axis of the inside cover 1050.

Referring to FIG. 11, electrically conductive pads 1064, 1066 may be removably placed in contact with the electrodes 1074, 1076 and exposed through the two apertures of the inside cover 1050. The electrically conductive pads 1064, 1066 are positioned over the foot muscles and may be electrically and/or mechanically connected to the electrodes 1074, 1076 of the circuit 1070. The first aperture 1060 (arch aperture) is located near an arch of the wearer's foot, and the first electrically conductive pad 1064 (arch pad) may be placed in the arch aperture 1020. The second aperture 1062 (heel aperture) is located near a heel of the foot, and the second electrically conductive pad 1066 (heel pad) may be placed in the heel aperture 1022.

When attached to the electrodes 1074, 1076 of the circuit 1070, the electrically conductive pads 1064, 1066 are electrically connected to the electrodes 1074, 1076. When touching the skin of the foot, the pads 1064, 1066 electrically connected to the wearer's foot. The pads 1064, 1066 comprise a support layer and may further comprise a protective film on each side of the pads. The pads 1064, 1066 may further comprise electrically conductive gel to enhance their electrical conductivity. The outside surfaces of the pads 1064, 1066 may be covered by adhesive so that the pads 1064, 1066 are removably attached to the electrodes. The inside surfaces of the electrically conductive pads 1064, 1066 touch the skin of the wearer's foot when the wearable device 1000 is worn. Electrical stimulation conducts from the electrodes 1074, 1076 to the wearer's foot via the pads 1064, 1066. For a wearable device 1000 without pads 1064, 1066, electrical stimulation may directly conduct from the electrodes 1074, 1076 to the foot.

The ankle portion 1056 of the inside cover 1050 is attached to the ankle portion 1006 of the outside cover 1002.

The circuit 1070 (FIG. 10) is positioned between the outside cover 1002 and the inside cover 1050 and conducts electricity from a control, which generates electrical stimulation, to the wearer's foot. The circuit 1070 comprises first and second connectors 1072, arch electrode 1074, heel electrode 1076, and conductors 1078 such as wired or conductive traces. Optionally, the electrically conductive pads 1064, 1066 are electrically connected to the control via the circuit 1070.

The connectors 1072 electrically connect the control with the circuit 1070. The circuit 1070 is made out of electrically conductive materials. The connectors 1072 may be located on the outside surface of the outside cover 1002 or the inside surface of the inside cover 1050.

The connectors 1072 may electrically or both electrically and mechanically connect the control with the circuit 1070. The control may removably attach to the connectors 1072. The connectors 1072 may be one or more snaps, clips, slides, pins, or others known in the art.

In addition to first and second connectors 1072, one or two or more additional connectors 1073 may be provided for additional electrical and or mechanical connection to a control. In the illustrated embodiment, first and second connectors 1072 are configured to both electrically and mechanically removably connect to the housing of the control. Additional mechanical integrity is provided by the third connector 1073 which mechanically releasably connects to the housing of the control. See also FIG. 12.

Referring to FIG. 14, each of the arch electrode 1074 and the heel electrode 1076 may comprise a flexible, conductive foil. The conductive foil may comprise silver. The arch electrode 1074 is placed adjacent to the first aperture 1060 of the inside cover 1050 near an arch of the foot. The heel electrode 1076 is placed adjacent to the second aperture 1062 of the inside cover 1050 near a heel of the wearer's foot. The electrically conductive pads 1064, 1066 may be removably attached to the arch electrode 1074 and the heel electrode 1076.

The wires 1078 electrically connect the connectors 1072 with the arch electrode 1074 and the heel electrode 1076. The wire 1078 may comprise a conductive foil. Insulator 1080 is placed around the wires 1078 and electrically insulates the wires to prevent unwanted electrical leak from the wires 1078. It is desirable that electricity is conducted from the control to the circuit 1070 only via the connectors 1072, and electricity is conducted from the circuit 1070 to the skin of the foot only via the arch electrode 1074 and the heel electrode 1076. Protector 1082 is placed around the wires 1078 near the connectors 1072 and protects the wires 1078 from load, tension, stress, physical fatigue, or failure. The protector 1082 may be composed of materials whose stiffness is higher than that of the wires 1078. The protector 1082 may also be composed of insulating materials. The protector 1082 may be composed of the same materials as the insulator 1080.

Figure 15:
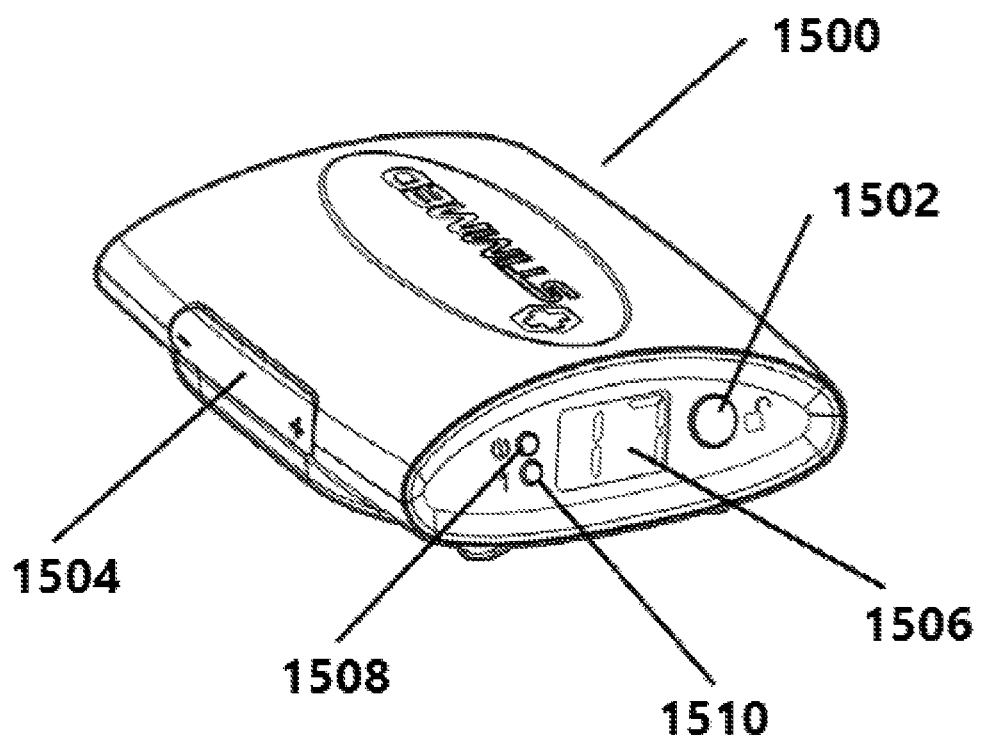
FIG. 15 shows a control that generates and modulates electrical stimulation, according to aspects of the present invention.

FIG. 15 shows a control 1500 for controlling administration of electrical stimulation. The control 1500 generates electrical stimulation signal, which is conducted to the wearer's foot via the connectors 1072, the wires 1078, the electrodes 1074, 1076, and, optionally, the removable pads 1064, 1066. The control 1500 may produce an intermittent signal pattern such as a square wave pattern of variable frequency, duration, intensity, ramp time, and stimulation on-off cycle. The control 1500 is programmed in a manner to stimulate the target muscles to reduce pooling of the blood in the soleal veins of the calf. While wearing the wearable device 1000, the wearer may modulate one or more characteristics of electrical impulses applied to the wearer, including the frequency, duration, intensity, ramp time, and on-off cycle of the electrical stimulation by operating the control 1500. Alternatively, the control 1500 may be preprogrammed or programmed once during an initial setup process.

In one aspect of the present invention, the control 1500 may comprise a power controller 1502 and a stimulation adjuster 1504. The power controller 1502 turns the control 1500 on and off. The power controller 1502 may be one or more buttons, keypads, switches, dials, slides, or levers. The stimulation adjuster 1504 controls one or more the characteristics of the electrical stimulation, including the frequency, duration, intensity, ramp time, and on-off cycle. The stimulation adjuster 1504 may be one or more buttons, keypads, switches, dials, slides, or levers. The control 1500 may further comprise a display screen 1506, which shows the characteristics of the electrical stimulation as the stimulation is adjusted by the stimulation adjuster 1504. The display screen 1506 may go to sleep after a certain period of inactivity. In another aspect of the present invention, the control 1500 may further comprise a power indicator 1508 and a stimulation indicator 1510. The power indicator 1508 indicates whether the power of the control 1500 is on or off. The power indicator 1508 may be a speaker, a light bulb, a LED, a display, a vibrator, or a motor. The stimulation indicator 1510 indicates whether the control 1500 is generating electrical stimulation. The stimulation indicator 1508 may be a speaker, a light bulb, a LED, a display, a vibrator, or a motor.

In one aspect of the present invention, the maximum or peak stimulation intensity may be between about 20 mA and about 40 mA and in one implementation is about 30 mA. The maximum frequency of the electrical stimulation may be between about 40 Hz and about 60 Hz and in one implementation is about 50 Hz. The maximum or peak voltage may be about 133V DC, and the maximum impedance may be about 5 kΩ. One example of stimulation signal pattern type may be a constant current, biphasic pulse. Constant current means that as the impedance of the control 1500 increases, the voltage of the control 1500 increases in order to maintain the set current. This only happens as long as the voltage is less than the maximum voltage. The output electrical stimulation is determined according to the following equation: $V=IZ$, where V is the voltage, I is the current, and Z is the impedance of the control 1500.

In one aspect of the present invention, the duration of each cycle of the electrical stimulation may be about 300 microseconds (or about 150 microseconds per phase). The positive and negative phases of the electrical stimulation may be symmetrical to each other. If there is any asymmetry between the phases, such asymmetry is preferably less than 10% difference in area. The electrical asymmetry between the phases may result in electrical charge accumulation on one of the electrically conductive pads 1064, 1066 or the electrodes 1074, 1076 after each cycle of the electrical stimulation (or each pair of stimulation phases).

Figure 16A:
FIGS. 16A, 16B, and 16C show exemplary waveforms of electrical stimulation generated from a control, according to aspects of the present invention.
Figure 16B:
Figure 16C:

FIGS. 16A, 16B, and 16C show exemplary waveforms of electrical stimulation generated from the control 1500. Referring to FIG. 16A, the waveform output generated from the control 1500 is biphasic with 12 seconds of 50 Hz stimulation followed by 48 seconds of rest. The intensity of the electrical stimulation may change according to the one-minute cycle that includes 2 seconds of ramping up, 8 seconds of constant set intensity, 2 seconds of ramping down, and 48 seconds of rest. If the intensity of the electrical stimulation is increased, the change in the output waveform will be as shown in FIG. 16B. If the intensity of the stimulation is decreased, the change in the output waveform will be as shown in FIG. 16C.

Before wearing the wearable device 1000, the wearer may clean the area of the foot where the pads 1064, 1066 or the electrodes 1074, 1076 will be placed in order to allow good contact and to help prevent skin irritation. The wearer may use a mild soap and water to wash the skin of the foot before placing the pads 1064, 1066 or the electrodes 1074, 1076 on the skin to improve adhesion. It is preferred that the wearer applies the pads 1064, 1066 or the electrodes 1074, 1076 to clean, unbroken skin.

Figures 17A, 17B, 17C:
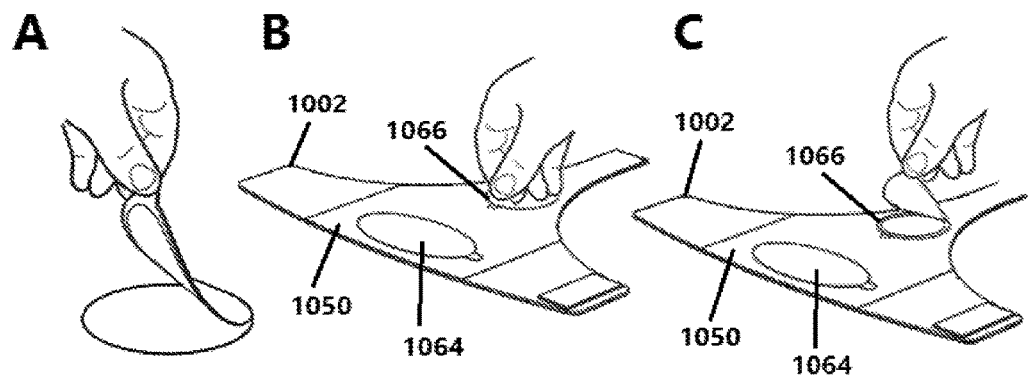
FIGS. 17A, 17B, and 17C show a procedure of attaching electrically conductive pads to a wearable device, according to aspects of the present invention.

FIGS. 17A, 17B, and 17C show a procedure of attaching the releasable electrically conductive heel pad 1066 (second electrically conductive pad) to the wearable device 1000. Referring to FIG. 17A, the wearer may peel the heel pad 1066 from the protective film on one side of the pad 1066. The wearer may alternatively peel the protective film from one side of the heel pad 1066. Referring to FIG. 17B, the wearer may then place the heel pad 1066 in the heel aperture 1022 (second aperture) of the inside cover 1050. Referring to FIG. 17C, the wearer may then peel the protective film from the foot contacting side of the heel pad 1066. The wearer may place the arch pad 1064 (first electrically conductive pad) to the wearable device 1000 in a similar fashion as described above.

Figures 18A, 18B, 18C, 18D, 18E, 18F:
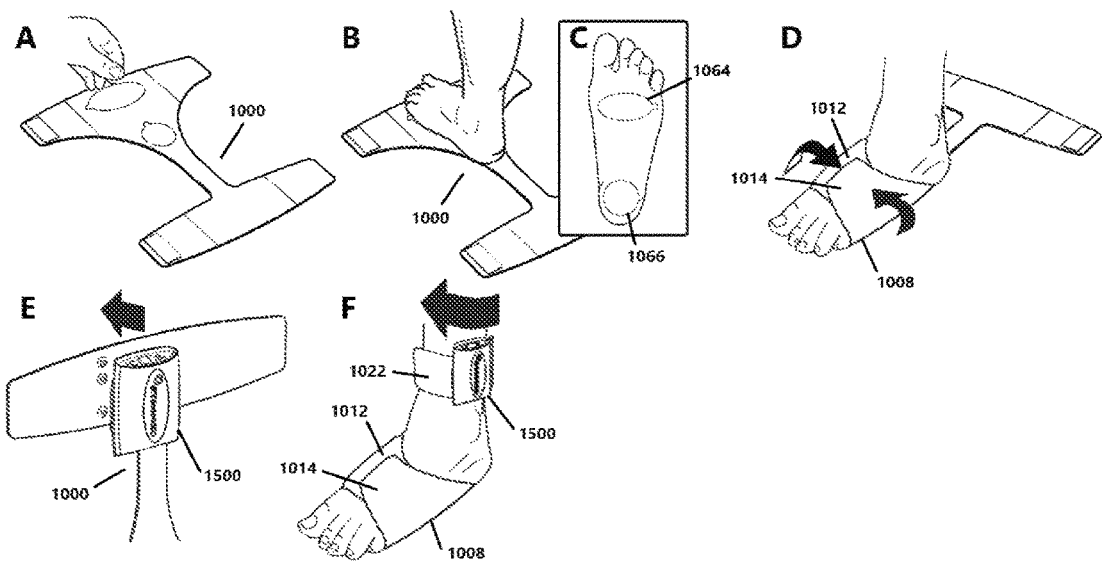
FIGS. 18A, 18B, 18C, 18D, 18E, and 18F show a procedure of mounting a wearable device and a control on a wearer's foot, according to aspects of the present invention.

FIGS. 18A, 18B, 18C, 18D, 18E, and 18F show a procedure of mounting the wearable device 1000 and the control 1500 on the wearer's foot. This procedure may occur after applying the electrically conductive pads 1064, 1066 to the wearable device 1000. Referring to FIGS. 18A and 18B, the wearer may step on the wearable device 1000 or place the wearable device 1000 on the wearer's foot. The wearer may place the arch pad 1064 attached to the wearable device 1000 near the arch of the wearer's foot and then place the heel pad 1066 attached to the wearable device 1000 near the heel of the wearer's foot. The wearer may alternatively place the heel pad 1066 near the heel of the wearer's foot and then place the arch pad 1064 near the arch of the wearer's foot. FIG. 18C shows where the arch pad 1064 and the heel pad 1066 may be placed on the wearer's foot.

Referring to FIG. 18D, the wearer may wrap the foot strap wings 1012, 1014 of the foot strap 1008 of the wearable device 1000 around the wearer's foot. The wearer may optionally use the foot strap fasteners 1016, 1618 to hold the two ends of the foot strap 1008 together. Referring to FIG.

18E, the wearer may attach the control 1500 to the wearable device 1000 using the connectors 1072 and optionally the additional connectors 1073. The wearer may attach the control 1500 to the wearable device 1000 before or after placing the electrically conductive pads 1064, 1066 to the wearable device 1000. The wearer may attach the control 1500 to the wearable device 1000 before, during, or after wearing the device 1000 on the foot.

Referring to FIG. 18F, the wearer may wrap the ankle strap wings 1020, 1022 of the ankle strap 1010 of the wearable device 1000 around the wearer's ankle. The wearer may optionally use the ankle strap fasteners 1024, 1026 to hold the two ends of the ankle strap 1010 together. The wearer may consult with a medical practitioner to set up the wearable device 1000 and the control 1500.

Once the wearable device 1000 and the control 1500 are placed on the wearer's foot, the wearer may turn on the control 1500 by operating the power controller 1502. The control 1500 may indicate via the display screen 1506, the power indicator 1508, and/or the stimulation indicator 1510 if the control 1500 is not connected to the wearable device 1000 when the control 1500 is turned on. After turning on the power of the control 1500, the wearer may increase the intensity of the electrical stimulation by operating the stimulation adjuster 1504. The wearer may feel an electrical sensation as the intensity of the electrical stimulation increases. The wearer may experience a visible curl of the wearer's toes as the intensity of the stimulation increases. The level of stimulation may vary from individual to individual. The wearer may decrease the intensity of the electrical stimulation by operating the stimulation adjuster 1504. The wearer may decrease the intensity of the stimulation through the stimulation adjuster 1504 when the wearer feels discomfort.

Before removing the control 1500 from the wearable device 1000, the wearer may reduce the intensity of the electrical stimulation to zero by operating the stimulation adjuster 1504 or turn the control 1500 off by operating the power controller 1502. The control is safe to remove from the wearable device 1000 when the intensity of the stimulation is zero or the control is turned off. The control 1500 may further comprise a safety module that locks the control 1500 to the wearable device 1000 when the control 1500 is turned on, and intensity of the electrical stimulation is not zero.

In one aspect of the present invention, the wearable device 1000 and the control 1500 may be ideally operated at temperature from 5° C. to 38° C., relative humidity from 15% to 93%, atmospheric pressure from 700 hPa to 1060 hPa, and altitude up to 3000 m above sea level.

The present invention has been described in relation to particular examples, which are intended to be illustrative rather than restrictive, with the scope and spirit of the invention being indicated by the following claims and their equivalents.

What is claimed is:

1. A wearable device for positioning at least two electrodes adjacent the sole of a wearer's foot, comprising:
a substantially I-shaped flexible support comprising:
a bottom portion configured to extend along a least a portion of the bottom of the foot, posteriorly from an arch;
an ankle portion of the support configured to extend upwardly along the back of the wearer's foot from the heel, wherein the ankle portion comprises a lateral edge and a medial edge, the lateral and medial edges of the ankle portion both being configured to be positioned along a posterior side of the wearer's leg;
a heel portion configured to extend around the heel, the heel portion joining the bottom portion to the ankle portion;
a foot strap carried by the support, the foot strap comprising two wings extending laterally from the bottom portion and being configured to attach to one another to secure the bottom portion to the bottom of the foot;
an ankle strap carried by the support, the ankle strap comprising two wings extending laterally from the lateral and medial edges of the ankle portion and being configured to extend from the posterior side of the wearer's leg entirely around a lower circumference of the wearer's leg to attach to one another so as to secure the ankle portion to the wearer's leg, wherein the substantially I shaped flexible support has a length extending from the foot strap to the ankle strap configured to position the ankle strap around a lower portion of the wearer's leg above the ankle; and
a posterior electrode and an anterior electrode carried by the bottom portion, the anterior electrode being positioned anteriorly to the posterior electrode;
wherein the bottom portion and the ankle portion are configured to lie flat adjacent one another such that the wearer may step onto the flexible support to position the wearer's foot over the posterior electrode and the anterior electrode, the heel portion configured to flex so that the ankle portion may extend upwardly from the bottom portion, and
wherein the two wings of the foot strap are configured to lie flat adjacent the bottom portion and the two wings of the ankle strap configured to lie flat adjacent the ankle portion.

2. A wearable device as in claim 1, wherein the bottom portion comprises a central longitudinal axis, and at least a portion of each of the posterior electrode and anterior electrode resides on both sides of the axis.

3. A wearable device as in claim 2, wherein each of the posterior electrode and anterior electrode has a geometric center and the geometric centers are within 0.5 inches of the longitudinal axis.

4. A wearable device as in claim 2, wherein the posterior electrode has a surface area of at least about 150% of the surface area of the anterior electrode.

5. A wearable device as in claim 2, wherein each of the posterior electrode and anterior electrode has a geometric center and the geometric centers are spaced apart along the axis by a distance within the range of from about 3 inches to about 5 inches.

6. A wearable device as in claim 5, wherein the geometric centers are spaced apart along the axis by a distance within the range of from about 3.5 inches to about 4.5 inches.

7. A wearable device as in claim 2, wherein each of the posterior electrode and anterior electrode intersects the axis.

8. A wearable device as in claim 2, wherein each of the posterior electrode and anterior electrode has a transverse axis, extending at a normal angle to the longitudinal axis, and the length of the anterior transverse axis is at least about 150% the length of the posterior transverse axis.

9. A wearable device as in claim 8, wherein the length of the anterior transverse axis is at least about 180% the length of the posterior transverse axis.

10. A wearable device as in claim 8, wherein the length of the posterior transverse axis is within a range of from about 1.5 inches to about 2.5 inches.

11. A wearable device as in claim 8, wherein the length of the anterior transverse axis is within the range of from about 3 inches to about 5 inches.

12. A wearable device as in claim 1, wherein each of the posterior electrode and anterior electrode further comprise a releasable electrically conductive pad.

13. A wearable device as in claim 1, wherein the support comprises a first surface for contacting the wearer and a second, opposing surface, and further comprising at least two electrical connectors on the second surface.

14. A wearable device as in claim 13, wherein the electrical connectors comprise mechanical connectors for both mechanically and electrically connecting to a removable control housing.

15. A wearable device as in claim 14, wherein the electrical connectors are carried by the ankle portion of the support.

16. A wearable device as in claim 14, further comprising a control carried by the electrical connectors.

17. A wearable device for positioning at least two electrodes adjacent the sole of a wearer's foot, comprising:
   a substantially I-shaped flexible support comprising:
      a bottom portion configured to extend along a least a portion of the bottom of the foot, posteriorly from an arch;
      an ankle portion of the support configured to extend upwardly along the back of the wearer's foot from the heel;
      a heel portion configured to extend around the heel, the heel portion joining the bottom portion to the ankle portion;
      a foot strap carried by the support, configured to secure the bottom portion to the bottom of the foot;
      an ankle strap carried by the support, configured to secure the ankle portion to the wearer's ankle; and
      a posterior electrode and an anterior electrode carried by the bottom portion, the anterior electrode being positioned anteriorly to the posterior electrode;
   wherein the bottom portion and the ankle portion are configured to lie flat adjacent one another such that the wearer may step onto the flexible support to position the wearer's foot over the posterior electrode and the anterior electrode, the heel portion configured to flex so that the ankle portion may extend upwardly from the bottom portion,
   wherein the bottom portion and the foot strap share a concave lateral curved edge and a concave medial curved edge,
      the concave lateral curved edge curving inward toward a medial direction as the concave lateral curved edge extends from the foot strap toward the heel portion and being configured to extend from the bottom of the foot around the lateral side of the foot and over the top of the foot, and
      the concave medial curved edge curving inward toward a lateral direction as the concave medial curved edge extends from the foot strap toward the heel portion and being configured to extend from the bottom of the foot around the medial side of the foot and over the top of the foot.

18. A wearable device as in claim 17, wherein the posterior electrode is positioned between the lateral curved edge and the medial curved edge.

19. A wearable device for positioning at least two electrodes adjacent the sole of a wearer's foot, comprising:
   a substantially I-shaped flexible support comprising:
   a bottom portion configured to extend along at least a portion of the bottom of the foot, posteriorly from an arch, and around the heel;
   an ankle portion of the support configured to extend upwardly along the back of the wearer's foot from the heel;
   a foot strap carried by the support, the foot strap comprising two wings extending laterally from the bottom portion configured to secure the bottom portion to the bottom of the foot;
   an ankle strap carried by the support, the ankle strap comprising two wings extending laterally from the ankle portion configured to secure the ankle portion to the wearer's ankle; and
   a posterior electrode and an anterior electrode carried by the bottom portion, the anterior electrode being positioned anteriorly to the posterior electrode;
   wherein the ankle portion comprises a width extending from a medial edge of the ankle portion to a lateral edge of the ankle portion, the width of the ankle portion being less than a width of the posterior electrode and less than a width of the anterior electrode.

* * * * *

UNITED STATES PATENT AND TRADEMARK OFFICE
CERTIFICATE OF CORRECTION

PATENT NO. : 10,213,593 B2
APPLICATION NO. : 15/287531
DATED : February 26, 2019
INVENTOR(S) : Kaplan et al.

Page 1 of 1

It is certified that error appears in the above-identified patent and that said Letters Patent is hereby corrected as shown below:

In the Specification

Column 7, Line 5, change "a" to --at--.

Column 10, Line 46, change "a" to --at--.

Column 10, Line 50, change "a" to --at--.

Column 12, Line 42, change "and or" to --and/or--.

In the Claims

Column 15, Line 61, in Claim 1, change "along a" to --along at--.

Column 16, Line 20, in Claim 1, change "I shaped" to --I-shaped--.

Column 17, Line 26 (Approx.), in Claim 17, change "along a" to --along at--.

Signed and Sealed this
Third Day of September, 2019

Andrei Iancu
*Director of the United States Patent and Trademark Office*